(12) United States Patent
Hochman et al.

(10) Patent No.: US 6,196,226 B1
(45) Date of Patent: Mar. 6, 2001

(54) METHODS AND APPARATUS FOR OPTICALLY IMAGING NEURONAL TISSUE AND ACTIVITY

(75) Inventors: Daryl Hochman; Michael M. Haglund, both of Seattle, WA (US)

(73) Assignee: University of Washington, Seattle, WA (US)

( * ) Notice: Subject to any disclaimer, the term of this patent is extended or adjusted under 35 U.S.C. 154(b) by 0 days.

(21) Appl. No.: 08/474,754

(22) Filed: Jun. 7, 1995

Related U.S. Application Data

(63) Continuation-in-part of application No. 08/073,353, filed on Jun. 7, 1993, now Pat. No. 5,465,718, which is a continuation-in-part of application No. 07/894,270, filed on Jun. 8, 1992, now Pat. No. 5,438,989, which is a continuation-in-part of application No. 07/565,454, filed on Aug. 10, 1990, now Pat. No. 5,215,095.

(51) Int. Cl.⁷ .................................................. A61B 5/05

(52) U.S. Cl. ................. 128/653.1; 128/664; 128/665; 128/633

(58) Field of Search .................. 128/633, 653.1, 128/664, 665, 741; 364/413.13

(56) References Cited

U.S. PATENT DOCUMENTS

| | | | |
|---|---|---|---|
| 4,543,604 | 9/1985 | Grosse | 358/111 |
| 4,570,638 | 2/1986 | Stoddart et al. | 128/665 |
| 4,736,307 * | 4/1988 | Salb | 364/413.05 |
| 4,768,516 | 9/1988 | Stoddart et al. | 128/665 |
| 4,811,414 | 3/1989 | Fishbine et al. | 382/52 |
| 4,972,331 | 11/1990 | Chance | 364/550 |
| 5,042,494 * | 8/1991 | Alfano | 128/665 |
| 5,131,398 * | 7/1992 | Alfano et al. | 128/665 |
| 5,187,672 | 2/1993 | Chance et al. | 364/550 |
| 5,198,977 * | 3/1993 | Salb | 128/633 |
| 5,353,799 | 10/1994 | Chance | 128/664 |
| 5,369,496 * | 11/1994 | Alfano et al. | 128/665 |
| 5,413,108 * | 5/1995 | Alfano | 128/665 |
| 5,482,034 | 1/1996 | Lewis et al. | 128/633 |
| 5,507,287 * | 4/1996 | Palcic et al. | 128/665 |
| 5,584,296 | 12/1996 | Ciu et al. | 128/633 |

FOREIGN PATENT DOCUMENTS

| | | | |
|---|---|---|---|
| 8300970 | 3/1983 | (WO) | H04N/5/32 |

OTHER PUBLICATIONS

G. Gratton et al., Rapid Changes of Optical Parameters in the Human Brain During a Tapping Task, *Journal of Cognitive Neuroscience* 7:4, pp. 446–456, 1995.

Haglund et al., Optical imaging of epileptiform and functional activity in human cerebral cortex, Nature 358:668–671, Aug. 20, 1992.

Hill et al., Opacity Changes in Stimulated Nerve, J.Physiol. 108:278–281, 1949.

Ojemann, Functional Mapping of Cortical Language Areas in Adults, Intraoperative Approaches, Raven Press, Ltd., New York, 1993.

L.B. Cohen et al., Light Scattering and Birefringence Changes during Nerve Activity, Nature 218: 438–441, 1968.

(List continued on next page.)

Primary Examiner—Brian L. Casler
(74) *Attorney, Agent, or Firm*—Ann W. Speckman; Janet Sleath

(57) ABSTRACT

The present invention provides a method and apparatus for distinguishing neuronal tissue from surrounding tissue, for distinguishing functional neuronal tissue from dysfunctional tissue, and for imaging of functional neuronal areas in cerebral cortex by detecting changes in the optical properties of the neuronal tissue following stimulation of neuronal activity.

27 Claims, 17 Drawing Sheets

(2 of 17 Drawing Sheet(s) Filed in Color)

OTHER PUBLICATIONS

Lipton, Effects of Membrane Depolarization on Light Scattering by Cerebral Cortical Slices, J. Physiol. 231:365–383, 1973.

Lewis et al., NADH Fluorescence and $[K^+]_o$ Changes During Hippocampal Electrical Stimulation, 405–417, 1974.

Grinvald et al., Functional architecture of cortex revealed by optical imaging of intrinsic signals, Nature 324: 361–364, 1986.

Inoue, Video Microscopy, Plenum Press, 309–392, New York and London, 1986.

Yodh et al., Spectroscopy and Imaging with Diffusing Light, Physics Today, 34–40, Mar. 1995.

Benaron et al., Optical Time–of–Flight and Absorbance Imaging of Biologic Media, Science 259: 1463–1466, Mar. 5, 1993.

Chance et al., Highly senstive object location in tissue models with linear in–hase and anti–phase multi–element optical arrays in one and two dimensions, Proc. Natl. Acad. Sci. 90: 3423–3427, Apr. 1993.

Kinsey et al., Endoscopic System for simultaneous visual examination and electronic detection of fluorescence, Rev.Sci.Instrum. 51:10, 1403–06, 1980.

Dougherty et al., Photoradiation Therapy for the Treatment of Malignant Tumors Cancer Research 38, 2628–33, 1978.

Doiron et al., Fluorescence Branchoscopy for Detection, Chest 76:1, 27–32, 1979.

Palcic et al., Development of a Lung Imaging Fluorescence Endoscope, Annual Intl.Conf. of IEEE Engrng in Medicine & Biology Society 12:1, 0196–97, 1990.

Baumgartner et al., A Fluorescence Imaging Device for Endoscopic Detection of Early Stage Cancer—Instrumental and Experimental Studies, Pergamon Journals Ltd., 513–517, 1990.

* cited by examiner

Fig. 2A2
Fig. 2B2
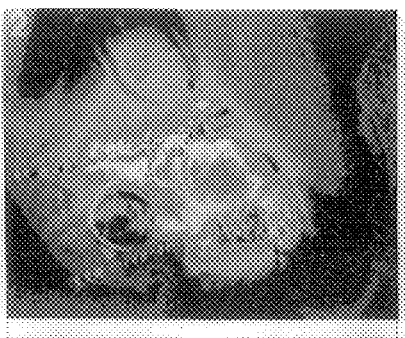
Fig. 2C2
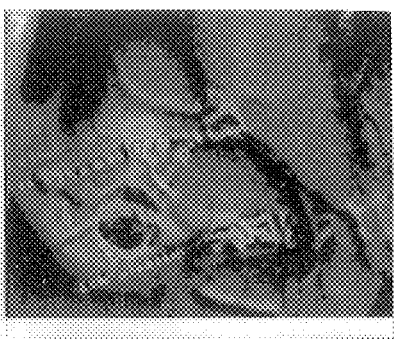
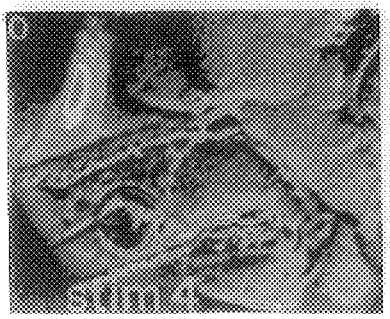
Fig. 2A4
Fig. 2B4
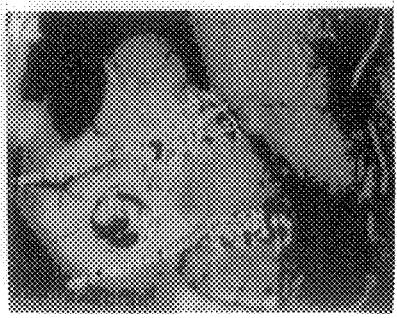
Fig. 2C4

Fig. 4A 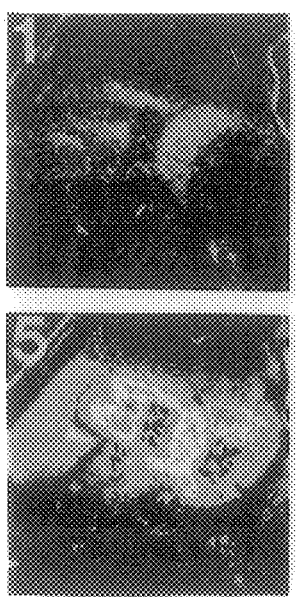 Fig. 4B  Fig. 4C  Fig. 4D 
Fig. 4E  Fig. 4F  Fig. 4G  Fig. 4H Fig. 6A1  Fig. 6A2  Fig. 6A3
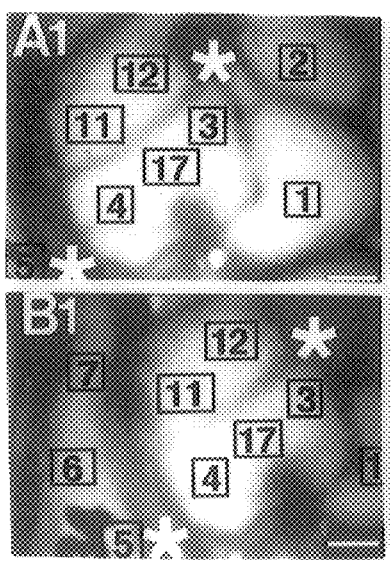 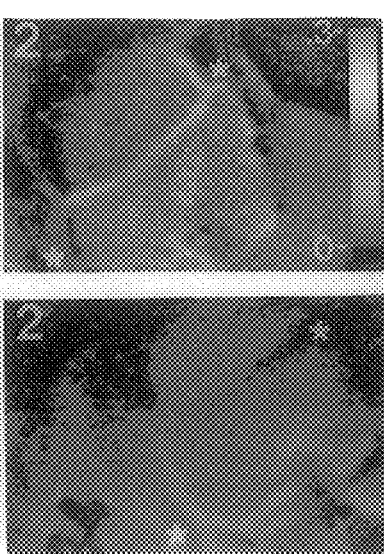 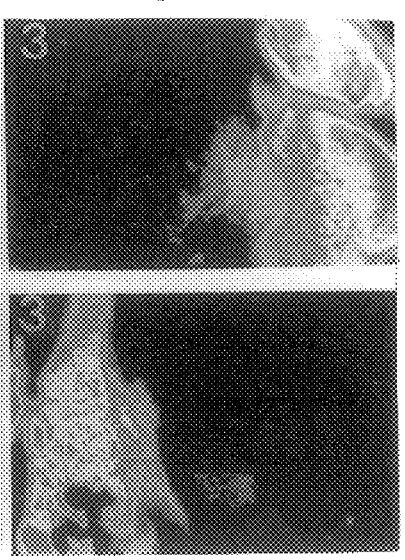
Fig. 6B1  Fig. 6B2  Fig. 6B3

Fig. 8A
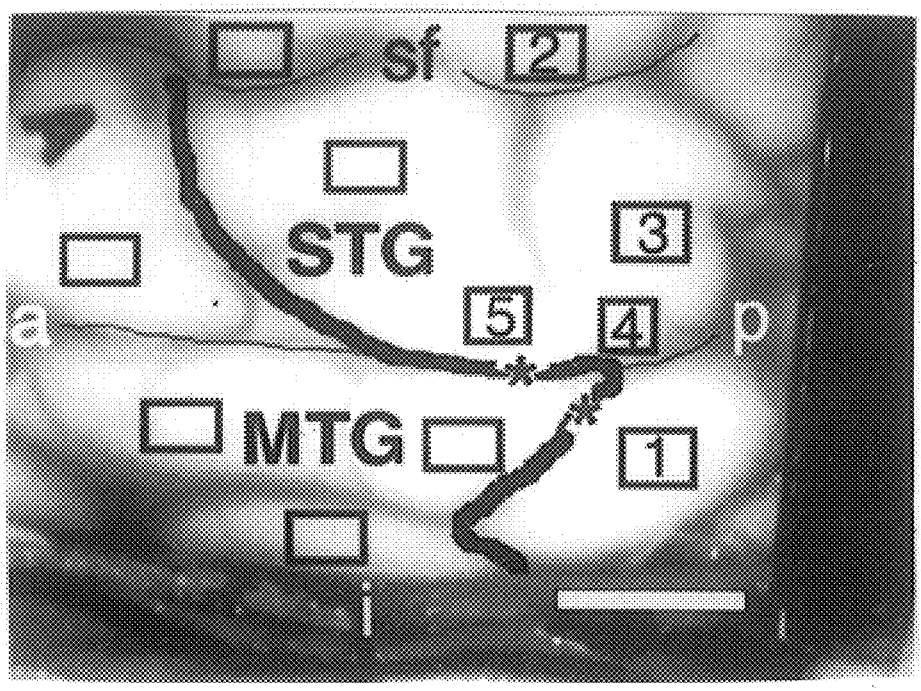
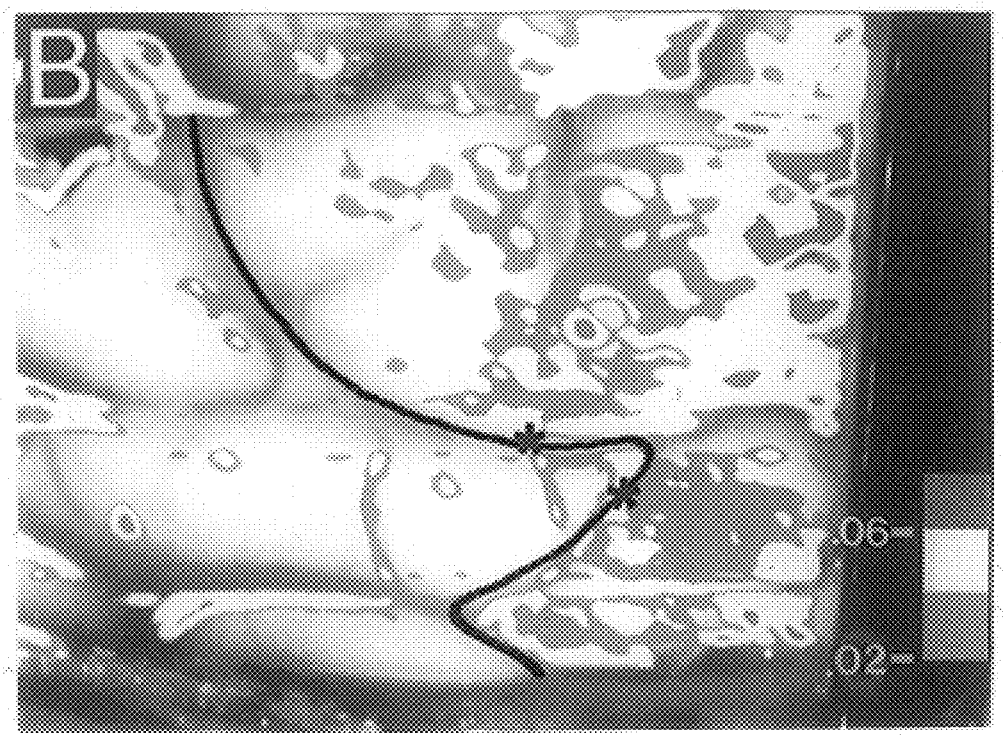
Fig. 8B

FIG. 13A1
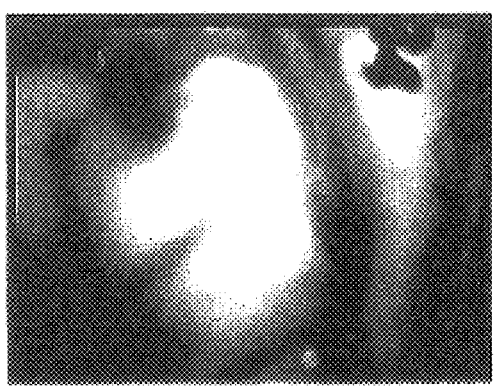
FIG. 13B1
FIG. 13A2
FIG. 13B2
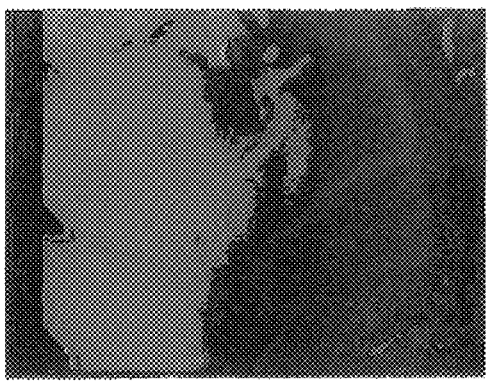

METHODS AND APPARATUS FOR OPTICALLY IMAGING NEURONAL TISSUE AND ACTIVITY

CROSS REFERENCE TO RELATED APPLICATIONS

This patent application is a continuation-in-part of U.S. patent application Ser. No. 08/073,353, filed Jun. 7, 1993 and issued as U.S. Pat. No. 5,465,718, which is a continuation-in-part of U.S. patent application Ser. No. 07/894,270, filed on Jun. 8, 1992 and issued as U.S. Pat. No. 5,438,989, which is a continuation-in-part of U.S. patent application Ser. No. 07/565,454 filed on Aug. 10, 1990 and issued as U.S. Pat. No. 5,215,095, all of which are incorporated herein by reference in their entirety.

TECHNICAL FIELD OF THE INVENTION

The present invention relates to methods and apparatus for optically imaging neuronal tissue and the physiological events associated with neuronal activity. The methods and apparatus of the present invention may be used for optically imaging and mapping functional neuronal activity, differentiating neuronal tissue from non-neuronal tissue, identifying and spatially locating dysfunctional neuronal tissue, and monitoring neuronal tissue to assess viability, function and the like.

BACKGROUND OF THE INVENTION

Many experimental techniques have been applied to study the physiology of the nervous system. Several of those techniques are described below. One of the applications for which the development of such techniques is essential is to assist a surgeon during surgery to avoid or reduce damage to functional neuronal tissue. Techniques currently used for diagnostic and intraoperation assessment are also described below.

Hill and Keynes observed that the nerve from the walking leg of the shore crab (*Carcinus maenas*) normally has a whitish opacity caused by light scattering, and that opacity changes evoked by electrical stimulation of that nerve were measurable. Hill, D. K. and Keynes, R. D., "Opacity Changes in Stimulated Nerve," J. Physiol. 108:278–281 (1949). Since the publication of those results, experiments designed to learn more about the physiological mechanisms underlying the correlation between optical and electrical properties of neuronal tissue and to develop improved techniques for detecting and recording activity-evoked optical changes have been ongoing.

Several types of phenomenon relating to physiological neuronal activity have been detected. Thermographic studies have detected thermal radiation changes that take place during neuronal activation using infrared imaging techniques. Spectrophotometric techniques have been used to detect changes in absorption of the oxidizable fraction of cytochrome oxidase in brain tissue. Spectroscopic techniques such as electron microscopy and x-ray diffraction are not well-suited to studying physiological activity in living neuronal tissue because of the high risk of tissue damage.

Many biomolecules fluoresce as a result of excitation with emr at the wavelength of the molecule's absorption band. This excitation causes the molecule to emit part of the absorbed energy at a different wavelength, and the emission can be detected using fluorometric techniques. Most physiological studies measuring intrinsic fluorescence have selected for NADH, which is an important intermediate in oxidative catabolism. Furthermore, NADH concentration in neuronal tissue is believed to be correlated with neuronal activity. Upon excitation with ultraviolet light, NADH fluoresces at about 460 nm. Unfortunately, this technique would not be suitable for monitoring neuronal activity in humans, because illumination of in vivo neuronal tissue in vivo with ultraviolet light may cause serious tissue damage.

Another technique for detecting neuronal activity involves administration of a voltage-sensitive dye, whose optical properties change during changes in electrical activity of neuronal cells. The spatial resolution achieved by this technique is near the single cell level. For example, researchers have used the voltage-sensitive dye merocyanine oxazolone to map cortical function in a monkey model. Blasdel, G. G. and Salama, G., "Voltage Sensitive Dyes Reveal a Modular Organization Monkey Striate Cortex," *Nature* 321:579–585, 1986. However, the use of these kinds of dyes would pose too great a risk for use in humans in view of their toxicity. Furthermore, such dyes are bleached by light and must be infused frequently.

Intrinsic changes in optical properties of cortical tissue have been assessed by reflection measurements of tissue in response to electrical or metabolic activity. Grinvald, A., et al., "Functional Architecture of Cortex Revealed by Optical Imaging of Intrinsic Signals," *Nature* 324:361–364, 1986. Grinvald, et al., "Optical Imaging of Neuronal Activity, Physiological Reviews, Vol. 68, No. 4, October 1988. Grinvald and his colleagues reported that some slow signals from hippocampal slices could be imaged using a CCD camera without signal averaging.

A CCD camera was used to detect intrinsic signals in a monkey model. Ts'o, D. Y., et al., "Functional Organization of Primate Visual Cortex Revealed by High Resolution Optical Imaging," *Science* 249:417–420, 1990. The technique employed by Ts'o et al. would not be practical for human clinical use, since imaging of intrinsic signals was achieved by implanting a stainless steel optical chamber in the skull of a monkey and contacting the cortical tissue with an optical oil. Furthermore, in order to achieve sufficient signal to noise ratios, Ts'o et al. had to average images over periods of time greater than 30 minutes per image.

Optically imaging neuronal and other types of tissue using techniques and apparatus similar to those described herein is described in U.S. Pat. No. 5,215,095, allowed U.S. patent application Ser. No. 5,438,989, and allowed U.S. patent application Ser. No. 5,465,781, which are incorporated herein by reference in their entirety.

The mechanisms responsible for intrinsic signals are not well understood. Possible sources of intrinsic signals include dilation of small blood vessels, neuronal activity-dependent release of potassium, and swelling of neurons and/or glial cells caused, for example, by ion fluxes or osmotic activity. Light having a wavelength in the range of 500 to 700 nm may also be reflected differently between active and quiescent tissue due to increased blood flow into regions of higher neuronal activity. Yet another factor which may contribute to intrinsic signals is a change in the ratio of oxyhemoglobin and deoxyhemoglobin in blood.

One of the important applications for quantitative techniques that identify and assess neuronal tissue and function, both in the central and the peripheral nervous system, is to provide information to medical professionals prior to and during surgery. A neurosurgeon attempts to map boundaries of dysfunctional tissue, so that dysfunctional tissue is removed without affecting the surrounding tissue, and as much neuronal function as is possible is preserved. Neurological surgery is especially risky, and precise resection of dysfunctional tissue without removing functional tissue is critical. It is also important for surgeons working outside the central nervous system to locate peripheral nerves and avoid damaging them during other types of surgical procedures.

Current intraoperative techniques do not provide rapid or high resolution differentiation of dysfunctional neuronal tissue from normal neuronal tissue, or of neuronal tissue from surrounding tissue. Presently, electroencephalography (EEG) and electrocorticography (ECoG) techniques are used prior to and during neurosurgery for the purposes of identifying areas of abnormal neuronal activity. These measurements provide a direct measurement of the electrical activity in neuronal tissue.

One type of neurosurgical procedure which exemplifies these principles is the surgical treatment of intractable epilepsy (that is, epilepsy which cannot be controlled with medications). EEG and ECoG techniques are typically used to identify epileptic foci. Intraoperative EEG techniques involve placing an array of electrodes upon the surface of the cortex to detect electrical activity. This is done in an attempt to localize abnormal cortical activity of epileptic seizure discharge.

Although EEG techniques are of widespread use, hazards and limitations are associated with these techniques. The size of the electrode surface and the distance between electrodes in an EEG array are large with respect to the size of brain cells (e.g., neurons) with epileptic foci. Thus, current techniques provide poor spatial resolution (approximately 1.0 cm) of the areas of abnormal cortical activity. Further, EEG techniques do not provide a map of normal cortical function in response to external stimuli (such as being able to identify a cortical area dedicated to speech function by recording electrical activity while the patient speaks). A modification of this technique, called cortical evoked potentials, can provide some functional cortical mapping. However, the cortical evoked potential technique suffers from the same spatial resolution problems as the EEG technique.

The most common method of intraoperative localization of cortical function during neurosurgery is direct electrical stimulation of the cortical surface with a stimulating electrode. Using this technique, the surgeon attempts to evoke either an observed motor response from specific parts of the body, or in the case of an awake patient, to generate specific sensations or cause an interruption in the patient's speech output. Again, this technique suffers from the same problems as the EEG technique because it offers only crude spatial localization of function.

Possible consequences of the inaccuracies of all these techniques when employed, for example, to identify the portion of the cortex responsible for epileptic seizures, are either that a greater than necessary amount of cortical tissue is removed, possibly leaving the patient with a deficit in function, or that not enough tissue is removed, leaving the patient uncured by the surgery. Despite these inadequacies, such techniques have been deemed acceptable treatment for intractable epilepsy.

A need in the art remains for methods and apparatus for optically imaging neuronal tissue which can precisely and quickly distinguish functional and dysfunctional (e.g., viable and nonviable) neuronal tissue, distinguish neuronal tissue from surrounding non-neuronal tissue, and map cortical neuronal function. Quantitative techniques providing the following capabilities would be desirable for assessing neuronal tissue: the ability to provide electrophysiological information with a high degree of spatial and temporal resolution; the ability to monitor the activity of single neurons, as well as patterns of activity in larger areas of neuronal tissue, and the property of being physiologically non-invasive, i.e., providing data without requiring application of chemicals or penetration of mechanical devices, such as neuroelectrodes.

SUMMARY OF THE INVENTION

The methods and apparatus described herein can be used to identify areas of neuronal activity during surgical or diagnostic procedures, and to monitor neuronal activity to assess tissue viability, function, recovery, degeneration and the like. For example, optical imaging techniques of the present invention can be used by a surgeon intraoperatively to distinguish between functional and dysfunctional neuronal tissue, or to distinguish between neuronal tissue and surrounding non-neuronal tissue. In addition, the methods and apparatus of the present invention can be used to identify neuronal tissue dedicated to important functions such as vision, movement, sensation, memory and language with a high degree of spatial resolution. Similarly, the methods and apparatus of the present invention can be used to detect areas of "abnormal" neuronal activity, whether that neuronal activity is unusually "high" or "low," such as epileptic foci ("high") or non-viable neuronal tissue ("low"). The present invention can also be used to identify and locate individual nerves, for example, during neurosurgical procedures involving anastomoses of severed nerves or during other types of surgery involving peripheral tissue, enabling the surgeon to avoid damage to nerves. Although the optical imaging techniques disclosed herein are used principally for in vivo applications, they may be used to monitor and assess neuronal activity for in vitro preparations as well. The optical imaging techniques can be used to provide information in "real time" and therefore can be employed intraoperatively.

The apparatus of the present invention employs an electromagnetic radiation (emr) source for uniformly illuminating an area of interest, and an optical detector capable of detecting and acquiring data relating to one or more optical properties of an area of interest. In a simple form, the apparatus of the present invention may include an optical fiber operably connected to an emr source that illuminates tissue, and another optical fiber operably connected to an optical detector, such as a photodiode, that detects one or more optical properties of the illuminated tissue. The detector is used to obtain control data representing the "normal" or "background" optical properties of an area of interest, and then to obtain subsequent data representing the optical properties of an area of interest during neuronal activity, e.g., stimulation of neuronal tissue, or during a monitoring interval. The subsequent data is compared to the control data to identify changes in optical properties representative of neuronal activity. According to a preferred embodiment, the control, subsequent and comparison data are presented in a visual format as images.

Various types of optical detectors may be used, depending on the optical property being detected, the format of data being collected, certain properties of the area of interest, and the type of application, e.g., surgery, diagnosis, monitoring, or the like. In general, any type of photon detector may be utilized as an optical detector. The optical detector generally includes photon sensitive elements and optical elements that enhance or process the detected optical signals. Numerous optical detectors are known and may be used or adapted for use in the methods and apparatus of the present invention.

Changes in optical properties that may be indicative of neuronal activity include, for example, reflection, refraction, diffraction, absorption, scattering, birefringence, refractive index, Kerr effect, and the like. The optical detection system may be incorporated in an apparatus for use external to the area of interest, or optical detection components may be mounted in an invasive or semi-invasive system, such as an endoscope, laparoscope or the like.

High resolution optical imaging of physical changes indicative of neuronal activity may be accomplished without using dyes or other types of contrast enhancing agents according to the methods and apparatus of the present invention, as evidenced by the examples described herein. The optical imaging techniques of the present invention are physiologically noninvasive, in that imaging of intrinsic signals does not require contacting the area of interest with any agents such as dyes, oils, devices, or the like. For particular applications, it may, however, be useful to administer contrast enhancing agents that amplify differences in an optical property being detected as a function of neuronal activity prior to acquiring subsequent data and generating a comparison. The use of contrast enhancing agents is described in detail, with reference to optical imaging of tumor and non-tumor tissue, in U.S. Pat. Nos. 5,438,989 and 5,465,781 which are incorporated by reference herein in their entirety. Suitable contrast enhancing agents include fluorescent and phosphorescent materials, dyes that bind to cell membranes, optical probes that preferentially accumulate in blood or in the intracellular space, phase resonance dye pairs, and the like. Detectors appropriate for use with such contrast enhancing agents are well known in the art.

Numerous devices for acquiring, processing and displaying data representative of one or more optical properties of an area of interest can be employed. One preferred device is a video camera that acquires control and subsequent images of an area of interest that can be compared to identify areas of neuronal activity or dysfunction. Examination of images provides precise spatial location of areas of neuronal activity or dysfunction. Apparatus suitable for obtaining such images have been described in the patents incorporated herein by reference and are more fully described below. For most surgical and diagnostic uses, the optical detector preferably provides images having a high degree of spatial resolution at a magnification sufficient to detect single neuronal cells or nerve fiber bundles. Several images are preferably acquired over a predetermined time period and combined, such as by averaging, to provide control and subsequent images for comparison.

Various data processing techniques may be advantageously used to assess the data collected in accordance with the present invention. Comparison data may be assessed or presented in a variety of formats. Processing may include averaging or otherwise combining a plurality of data sets to produce control, subsequent or comparison data sets. Images are preferably converted from an analog to a digital form for processing, and back to an analog form for display.

Data processing may also include amplification of certain signals or portions of a data set (e.g., areas of an image) to enhance the contrast seen in data set comparisons, and to thereby identify areas of neuronal activity and/or dysfunction with a high degree of spatial resolution. For example, according to one embodiment, images are processed using a transformation in which image pixel brightness values are remapped to cover a broader dynamic range of values. A "low" value may be selected and mapped to zero, with all pixel brightness values at or below the low value set to zero, and a "high" value may be selected and mapped to a selected value, with all pixel brightness values at or above the high value mapped to the high value. Pixels having an intermediate brightness value, representing the dynamic changes in brightness indicative of neuronal activity, may be mapped to linearly or logarithmically increasing brightness values. This type of processing manipulation is frequently referred to as a "histogram stretch" and can be used according to the present invention to enhance the contrast of data sets, such as images, representing changes in neuronal activity.

Data processing techniques may also be used to manipulate data sets to provide more accurate combined and comparison data. For example, patient movement, respiration, heartbeat, seizure or reflex activity may shift an area of interest during detection of optical properties and data collection. It is important that corresponding data points in data sets (such as corresponding areas of an image) are precisely aligned to provide accurate combined and comparison data. Such alignment may be accomplished manually by a practitioner having specialized skill and expertise, or using a variety of mathematical means. Optical markers may be fixed at an area of interest and detected as the data is collected to aid in manual alignment or mathematical manipulation. Various processing techniques are described below and in the patents incorporated herein by reference.

Inaccuracies and artifacts caused by patient movement during acquisition of data can be reduced by mechanical means. According to a preferred embodiment, the emr source and the optical detector are provided as an integral unit that is mountable to a patient during detection. Cranial posts are often provided when a patient has had substantial cortical involvement and may be used to mount an integrated emr source/detector unit for detecting or mapping cortical neuronal activity or function. Likewise, an integrated unit including an emr source and an optical detector may be mounted in a relatively "fixed" condition in proximity to other areas of interest. Alternatively, and particularly for neuronal monitoring applications, emr sources and/or optical detectors may be implanted in the area(s) of interest and operably connected to external data processing devices.

Comparison data may be displayed in a variety of ways. Comparison data may be displayed in a graphical format that highlights optical differences indicative of neuronal activity. A preferred technique for presenting and displaying comparison data is in the form of visual images or photographic frames corresponding to the area of interest. This format provides a visualizable spatial location (two- or three-dimensional) of neuronal activity and/or function that is useful for treatment, diagnosis and monitoring. To enhance and provide better visualization of contrast indicating neuronal activity or dysfunction, comparison images may be processed to provide an enhanced contrast grey scale or even a color image. A look up table ("LUT") may be provided, for example, that converts the gray scale values for each pixel to a different (higher contrast) gray scale value, or to a color value. Color values may map to a range of grey scale values, or color may be used to distinguish between positive-going and negative-going optical changes. In general, color-converted images provide higher contrast images that highlight changes in optical properties representing neuronal activity, function or dysfunction.

In operation, an area of interest in a patient is illuminated with electromagnetic radiation (emr) while one or a series of data points or data sets representing one or more optical properties of the area of interest is acquired during an interval of "normal" neuronal activity. This data represents the control, or background data. A series of data sets is preferably combined, for example by averaging, to obtain a control data set. The control data set is stored for comparison with data collected subsequently.

A subsequent data set representing the corresponding optical property is acquired during a subsequent time period. For monitoring applications, data may be collected at regular time intervals and monitored to detect aberrations from baseline values. For diagnostic or functional mapping applications, a subsequent data set is collected during a period of (anticipated) neuronal activity or inhibition. Neuronal activity or inhibition may be induced by a "natural" occurrence such as a seizure or stroke, or it may be induced by administering a paradigm to the patient to stimulate an intrinsic neuronal signal. Intrinsic neuronal signals may be induced by direct electrical stimulation of neuronal tissue (whether in the central or peripheral nervous system), or by motor activity, speech, thought, etc., that stimulates a specific cortical area. During a monitoring interval or stimulation of an intrinsic signal, one or a series of subsequent data sets, representing one or more of the detected optical properties of the area of interest, is acquired. A series of subsequent data sets is preferably combined, for example by averaging, to obtain a subsequent data set. The subsequent data set is compared with the control data set to obtain a comparison data set, preferably a difference data set. Comparison data sets can then be examined for evidence of changes in optical properties representative of neuronal activity or inhibition within the area of interest.

This technique can be used to identify areas of neuronal activity or dysfunction, and to accurately identify and map areas of specific neuronal function. Nerve dysfunction can be visualized and mapped as a portion of the nerve where an intrinsic signal from a stimulated nerve abruptly ends, or is altered, attenuated or diminished by comparing the control data to the subsequent data. Likewise, viable neuronal tissue can be distinguished from non-viable or nonfunctional neuronal tissue, and neuronal tissue can be distinguished from non-neuronal tissue. By employing the optical imaging techniques disclosed in this application, neuronal tissue can be monitored to detect changes in neuronal activity that take place during development, neuronal trauma (e.g., seizure, stroke, and the like), recovery from neuronal trauma, administration of therapeutic or diagnostic agents, and tissue transplantation and recovery. Comparison images may be acquired and displayed in "real-time" for use during surgery, or over a more prolonged period, such as during monitoring of neuronal tissue viability, diagnostic or therapeutic agents, trauma, recovery, and the like. The optical imaging techniques may also be used to assess neuronal tissue viability and function in vitro.

BRIEF DESCRIPTION OF THE DRAWINGS

This patent application contains at least one drawing executed in color. Copies of the patent with color drawings will be provided by the Patent and Trademark Office upon request and payment of the necessary fee.

The methods and apparatus of the present invention will be described in greater detail with reference to the figures described below that illustrate preferred embodiments.

FIG. 2 illustrates spatial images of stimulation-induced epileptiform activity. The images show comparisons between different degrees of activation illustrating both the spatial extent and amplitude of optical changes indicative of the extent of cortical activity. Specifically, FIG. 2 shows percentage difference images representative of various times during two of the stimulation trials described in Example 1. The top 3 images (2A2, 2B2, and 2C2) are from stimulation trial 2, where 6 mA cortical stimulation evoked a brief period of afterdischarge. These are compared to the bottom three images (2A4, 2B4, and 2C4), which are from stimulation trial 4, showing the optical changes evoked by cortical stimulation at 8 mA. FIGS. 2A2 and 2A4 compare control images during rest. FIGS. 2B2 and 2B4 compare the peak optical changes occurring during the epileptiform afterdischarge activity. FIGS. 2C2 and 2C4 compare the degree of recovery 20 seconds after the peak optical changes were observed. The magnitude of optical change is indicated by the gray-scale changes. Each image maps an area of cortex approximately 4 cm by 4 cm.

FIG. 4 illustrates a real-time sequence of dynamic changes of stimulation-evoked optical changes in human cortex. FIG. 4, panels 4A through 4H, show eight consecutive percentage difference images. Each image is an average of 8 frames (<¼ second per image). The magnitude of optical change is indicated by the gray-scale changes. Each image maps to an area of cortex that is approximately 4 cm by 4 cm. This FIG. demonstrates that the methods and apparatus of the present invention can be used to map, in real time, dynamics of optical changes, and display such information to a surgeon in an informative format.

FIG. 5 illustrates activation of somatosensory cortex by stimulation of a peripheral nerve in an anesthetized rat (inducing afferent sensory input by directly stimulating the sciatic nerve in the hind limb of a rat). The leftmost image.

FIG. 6 illustrates functional mapping of human language (Broca's area) and tongue and palate sensory areas in an awake human patient as described in Example 2. Images 6A1 and 6B1 are gray-scale images of an area of human cortex, with left being anterior, right-posterior, top-superior, and the Sylvan fissure on the bottom. The two asterisks on 6A1, 6B1, 6A2, and 6B2 serve as reference points for these images. The scale bars in the lower right corner of 6A1 and 6B1 are equal to 1 cm. In 6A1, the numbered boxes represent sites where cortical stimulation with electrical stimulating electrodes evoked palate tingling (1), tongue tingling (2), speech arrest-Broca's areas (3,4) and no response (11, 12, 17, 5, 6–7 premotor). Image 6A2 is a percentage difference control image of the cortex during rest in one of the tongue wiggling trials. The gray-scale bar on the right of 6A2 shows the relative magnitude of the gray values associated with images 6A2, 6A3, 6B2 and 6B3. Image 6A3 is a percentage difference map of the peak optical changes occurring during one of the tongue wiggling trials. Areas identified as tongue and palate sensory areas by cortical stimulation showed a large positive change. Suppression of baseline noise in surrounding areas indicated that, during the tongue wiggling trials, language-motor areas showed a negative-going optical signal. Image 6B2 is percentage difference control image of the cortex during one of the language naming trials. Image 6B3 is a percentage difference image of the peak optical change in the cortex during the language naming task. Large positive-going signals are present in Broca's area. Negative-going signals are present in tongue and palate sensory areas.

FIG. 7 shows time course and magnitude plots of dynamic optical changes in human cortex evoked in tongue and palate sensory areas and in Broca's area (language). This Figure shows the plots of the percentage change in the optical absorption of the tissue within the boxed regions shown in FIG. 6, images 6A1 and 6B1, during each of the three tongue wiggling trials and one of the language naming trials (see description of FIG. 6).

FIG. 8 illustrates an optical map of a cortical area important for language comprehension (Wernicke's area) in an awake human.

FIG. 8A shows the cortical surface of a patient where the anatomical orientation is left-anterior, bottom-inferior, with the Sylvan fissure running along the top. After optical imaging, all cortical tissue to the left of the thick line was surgically removed. Sites #1 and #2 were identified as essential for speech (e.g., cortical stimulation blocked ability of subject to name objects). At site #3, one naming error in 3 stimulation trials was found. As the surgical removal reached the area labeled by the asterisks on the thick line, the patient's language deteriorated. All the unlabeled sites in FIG. 8A had no errors while naming slides during cortical stimulation.

FIG. 8B shows an overlay of a percentage difference image over the gray-scale image of the cortex acquired during a language naming trial (see FIG. 6 for description of the language naming trial). The magnitude of the optical change is shown by the gray-scale bar on the lower right of the image.

FIG. 9 illustrates a time course and magnitude of dynamic optical changes in human cortex evoked in Wernicke's area (language comprehension).

FIG. 10D shows that 1 minute after dye injection, the normal tissue had cleared the dye, but dye was still retained in the tumor region. The concentration of dye in the center of this difference image was dye circulating in the sagittal sinus. Neuronal activity may likewise be imaged through other intact tissues, such as bone, duva, muscle, connective tissue, and the like.

FIG. 11 illustrates a grey-scale image of human cortex just anterior to face-motor cortex with one recording (R) and two stimulating (s) electrodes for applying stimulating current to induce epileptiform after discharge activity. Surface electrical signals were obtained by conventional EEG techniques. The cortex as illuminated with emr of wavelengths greater than about 690 nm and the images presented in FIGS. 6B–6E were acquired using a CCD camera as described herein. The images were processed to map regions of increasing (positive-going), decreasing (negative-going), and non-changing levels of cortical activity to the colors red, blue and black, respectively. Each image maps to an area of cortex that is approximately 4 cm by 4 cm.

FIGS. 11B–11E each correspond to an average of approximately 60 frames acquired at 30 Hz over a period of about 2 seconds.

FIG. 13 shows functional mapping of human language (Broca's area) and tongue and palate sensory areas in an awake human patient.

FIGS. 13A1 and 13B1 are gray-scale images of an area of human cortex with left being anterior, right-posterior, top-superior, and the Sylvan fissure on the bottom. The numeral 34 in FIG. 13A1 (partly obscured) serves as reference point to FIG. 13B1 in which the numeral is mostly obscured at the upper right edge of the Figure. Each image maps to an area of cortex that is approximately 4 cm by 4 cm.

FIGS. 13A2 and 13B2 are spatial maps of cortical activity in the areas of human cortex shown in FIGS. 12A1 and 12B1 during, respectively, a language naming exercise and a tongue wiggling exercise. The images were processed to map increasing, decreasing and constant levels of cortical activity in the colors red, blue and black, respectively.

DETAILED DESCRIPTION OF THE INVENTION

Figure 1A:
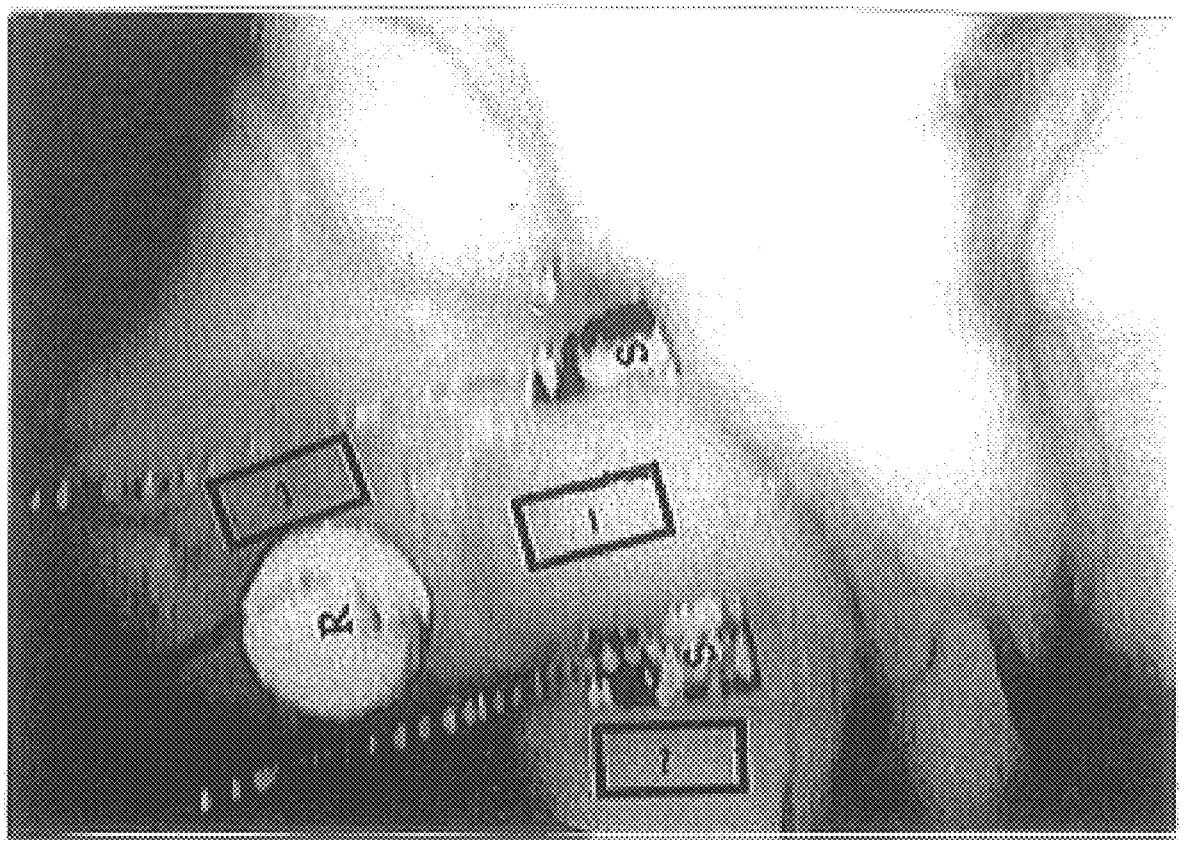
FIG. 1A illustrates a view of human cortex just anterior to face-motor cortex with one recording (R) and two stimulating (S) electrodes, and four sites (labeled 1, 2, 3, and 4) where average percent changes in corresponding optical properties were determined as described in Example 1.

Applicants' optical imaging methods and apparatus are described in greater detail below with reference to certain preferred embodiments. Certain aspects of the optical imaging technique have been described in even greater detail in the patents incorporated herein by reference. The detailed descriptions of certain preferred embodiments described herein are not intended to limit the scope of applicants' invention as set forth in the appended claims.

Definitions

The following terms, as used in this specification and the appended claims, have the meanings indicated:

Area of Interest is an area of tissue that comprises the subject of acquired data sets. The area of interest may, for example, be exposed tissue, tissue that underlies or is adjacent exposed tissue, or tissue cultured in vitro.

Arithmetic Loqic Unit (ALU) is a component that is capable of performing a variety of processing (e.g., mathematical and logic) operations (e.g., sum, difference, comparison, exclusive or multiply by a constant, etc.) on a data set.

Control Data is data representing one or more optical properties of the area of interest during a "normal" period or a predetermined period, such as prior to stimulation of an intrinsic signal. The control data set establishes a "background" level of neuronal activity for comparison with a subsequently acquired data set.

Charge Coupled Device (CCD) is a type of optical detector that utilizes a photo-sensitive silicon chip in place of a pickup tube in a video camera.

Comparison Data is data acquired by comparing subsequent data or data acquired at a particular time, with control data, such as by adding, subtracting, or the like. The comparison data set is used to identify and/or locate areas of neuronal activity.

Electromagnetic Radiation (emr) means energy having a wavelength of from about 450 to about 2500 nm. Emr illumination suitable for use in the optical imaging methods described herein is in the visible and infrared regions.

Frame is a digitized array of pixels.

Frame Buffer is a component that provides storage of a frame, such as a control image, a subsequent image or a comparison image.

Geometric Transformations can be used to modify spatial relationships between data points in a data set, such as pixels in an image. Geometric transformations are often called "rubber sheet transformations" because they can be viewed as the process of "printing" data, such as an image, on a sheet of rubber and stretching the sheet according to a predefined set of rules. As applied to video imaging, subsequent images can be viewed as having been distorted due to movement and it is desirable to "warp" these images so that they are spatially aligned with the control images. Geometric transformations are distinguished from "point transformations" in that point transformations modify a pixel's value in an image based solely upon that pixel's value and/or location, and no other pixel values are involved in the transformation. Geometric transformations are described in the publication *Digital Image Processing*, Gonzalez and Wintz, Addison-Wesley Publishing Co., Reading, 1987.

Image is a frame or composition of frames representing one or more optical properties of an area of interest.

Intrinsic Signal is a detectable change in one or more optical properties of neuronal tissue caused by physiologic activity. Intrinsic signals may be the related to membrane depolarization, glial cell swelling, ion flux across neuronal membranes, blood volume changes, blood oxygenation and deoxygenation tissue oxygenation and combinations thereof.

Optical properties relate to various properties detectable in the useful range of emr (450–2500 nm) including but not limited to scattering (Rayleigh scattering, reflection/retraction, diffraction, absorption and extinction), birefringence, refractive index, Kerr effect and the like.

Optical Detector is a device capable of detecting one or more desired optical properties of an area of interest. Suitable optical detectors include any type of photon detector, such as photodiodes, photomultiplier tubes, cameras, video cameras, CCD cameras, and the like.

Optical Imaging refers to the acquisition, comparison, processing and display of data representative of one or more optical properties of an area of interest that indicate neuronal activity. Optical imaging may involve acquisition processing and display of data in the form of images, but need not.

Paradigms cause a change in electrical activity of an area of neuronal tissue dedicated to a specific function, thus causing a change in neuronal activity reflected in the intrinsic signal. Ojemann, for example, has described paradigms which produce neuronal activity in areas of the cortex dedicated to such functions as speech, language, vision, etc. Ojemann, "Functional Mapping of Cortical Language Areas in Adults—Intra—operative Approaches," *Electrical and Magnetic Stimulation of the Brain and Spinal Cord*, edited by O. Devinsky, et al., Raven Press, Ltd., N.Y. N.Y. 1993. Administering a paradigm may also involve direct electrical stimulation of neuronal tissue.

Pixels are the individual units of an image in each frame of a digitized signal. The intensity of each pixel is linearly proportional to the intensity of illumination before signal manipulation and corresponds to the amount of emr (photons) being scattered from a particular area of tissue corresponding to that particular pixel. An image pixel is the smallest unit of a digital image and its output intensity can be any value. A CCD pixel is the smallest detecting element on a CCD chip and its analog output is linearly proportional to the number of photons it detects.

Subsequent Data is data representing one or more optical properties of an area of interest during a monitoring period or during or subsequent to stimulating an intrinsic signal.

Tissue means any cellular or multicellular mammalian component, whether or not it has a distinct structure or function. Neuronal tissue, for example, refers to individual neurons, bundles or collections of neurons, as well as highly organized cortex.

Apparatus

The inventive methods employ an apparatus comprising a source of high intensity emr, an optical detector for acquiring data representative of one or more optical properties of the area of interest, such as video signals, and image processing capability. The apparatus may be constructed as an integrated unit, or it may be used as a collection of components. The apparatus will be briefly described with reference to the schematic diagram, illustrated in FIG. 14, and various components and features will then be described in greater detail.

Figure 14:
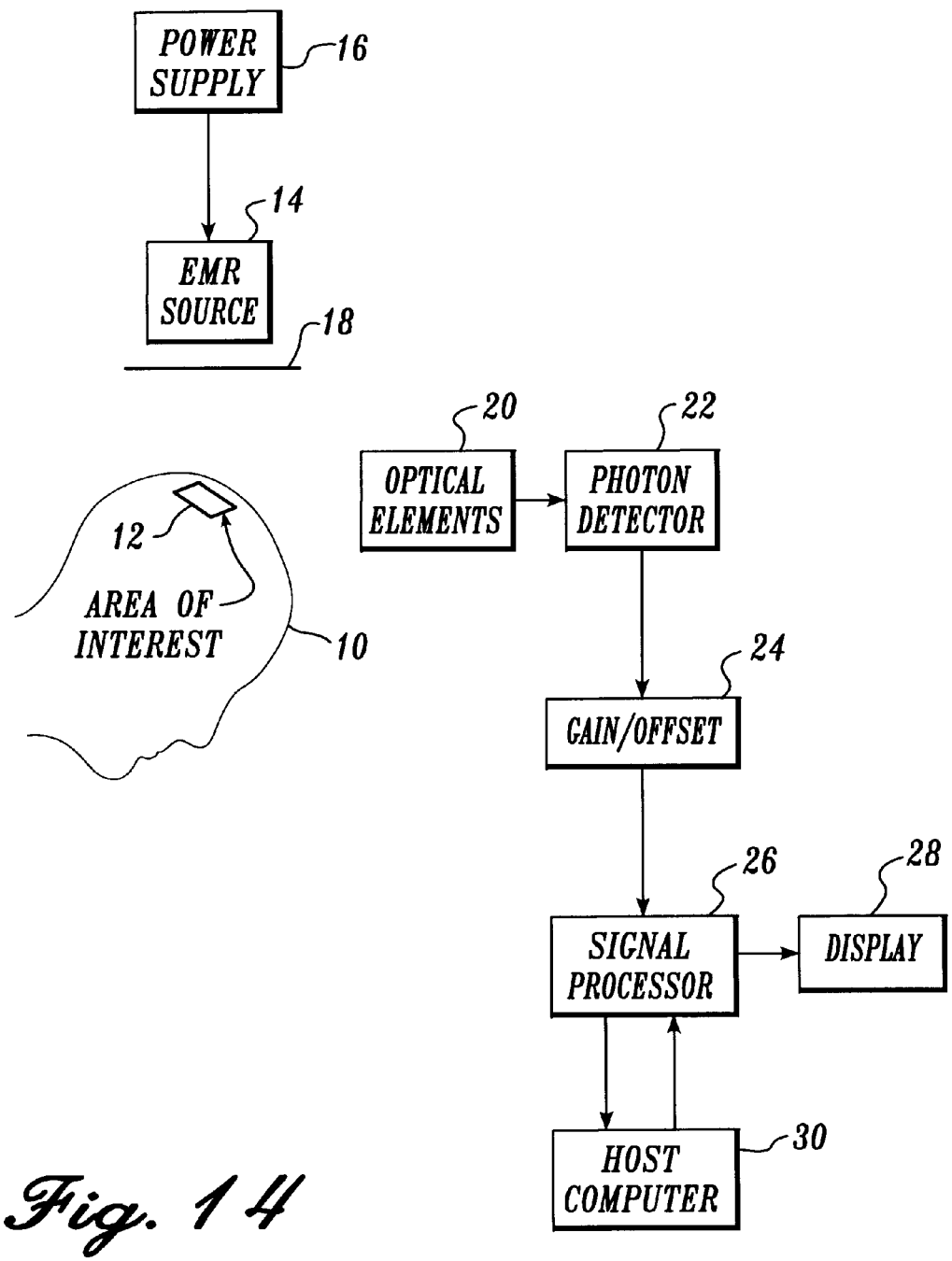
FIG. 14 is a simplified schematic diagram illustrating an apparatus of the present invention.

FIG. 14 illustrates a human patient 10 whose neuronal tissue represents area of interest 12. As is described in greater detail below, area of interest 12 may be fully or partially exposed, or imaging may be conducted through bone and/or dura with proper selection of emr wavelengths. During optical imaging, area of interest 12 is uniformly illuminated by emr source 14 powered by regulated power supply 16. Emr is preferably directed through an optical filter 18 prior to contacting area of interest 12.

During optical imaging, a light gathering optical element 20, such as a camera lens, endoscope, optical fibers and photon detector 22 or the like are placed to detect optical properties of area of interest 12. Signals representative of optical properties are processed, if desired, in a gain, offset component 24 and then conveyed to analog-to-digital (A/D) and digital signal processing hardware 26. Data representing optical properties and particularly changes in optical properties, are displayed on display device 28. The optical detection, display and processing components are controlled by host computer 30.

An emr source is used for illuminating the area of interest during acquisition of data representing one or more optical properties. In accordance with preferred methods of the present invention, the area of interest is typically cortical neuronal tissue or peripheral neuronal tissue. The emr source may be utilized to illuminate an area of interest directly, as when neuronal tissue is exposed during or in connection with surgery, or it may be utilized to illuminate an area of interest indirectly through adjacent or overlying tissue such as bone, dura, skin, muscle and the like.

The emr source employed in the present invention is preferably a high intensity, broad spectrum emr source, such as a tungsten-halogen lamp, laser, light emitting diode, or the like. Cutoff filters to selectively pass all wavelengths above or below a selected wavelength may be employed. A preferred cutoff filter excludes all wavelengths below about 695 nm. Preferred emr wavelengths for imaging intrinsic signals include, for example, wavelengths of from about 450 nm to about 2500 nm, and most preferably, wavelengths of the near infrared spectrum of from about 700 nm to about 2500 nm. Generally, longer wavelengths (e.g., approximately 800 nm) are employed to measure deeper cortical activity. Selected wavelengths of emr may also be used, for example, when various types of contrast enhancing agents are administered. The emr source may be directed to the area of interest by a fiber optic means. One preferred arrangement provides emr through strands of fiber optic using a beam splitter controlled by a D.C. regulated power supply (Lambda, Inc.).

The optical imaging methods of the present invention may also usefully employ non-continuous illumination and detection techniques. For example, short pulse (time domain), pulsed time, and amplitude modulated (frequency domain) illumination sources may be used in conjunction with suitable detectors (See, Yodh, A., and Chance, B. *Physics Today*, March, 1995). Frequency domain illumination sources typically comprise an array of multiple source elements, such as laser diodes, with each element modulated at 180° out of phase with respect to adjacent elements (see, Chance, B. et al., (1993) *Proc. Natl. Acad. Sci. USA*, 90, 3423–3427). Two-dimensional arrays, comprising four or more elements in two orthogonal planes, can be employed to obtain two-dimensional localization information. Such techniques are described in U.S. Pat. Nos. 4,972,331 and 5,187,672 which are hereby incorporated by reference.

Time-of-flight and absorbance techniques (Benaron, D. A. and Stevenson, D. K. (1993) *Science*, 259, 1463–1466) may also be usefully employed in the present invention. In yet another embodiment of the present invention, a scanning laser beam may be used in conjunction with a suitable detector, such as a photomultiplier tube, to obtain high resolution images of an area of interest.

Illumination with a part of the infrared spectrum allows for imaging intrinsic signals through tissue overlying or adjacent the area of interest, such as dura and skull. One exemplary infrared emr source suitable for imaging through tissue overlying or adjacent the area of interest is a Tunable IR Diode Laser from Laser Photonics, Orlando, Fla. When using this range of far infrared wavelengths, the optical detector is preferably provided as an infrared (IR) detector. IR detectors are made from materials such as indium arsenide, germanium and mercury cadmium telluride and are generally cryogenically cooled to enhance their sensitivity to small changes in infrared radiation. One example of an IR imaging system which may be usefully employed in the present invention is an IRC-64 infrared camera (Cincinnati Electronics, Mason, Ohio).

The area of interest must be evenly illuminated to effectively adjust the signal over a full dynamic range, as described below. Nonuniformity of illumination is generally caused by fluctuations of the illumination source and intensity variations resulting from the three-dimensional nature of the tissue surface. More uniform illumination can be provided over the area of interest, for example, by using diffuse lighting, mounting a wavelength cutoff filter in front of the optimal detector and/or emr source, or combinations thereof. Fluctuation of the illumination source itself is preferably addressed by using a light feedback mechanism to regulate the power supply of the illumination source. In addition, a sterile, optically transparent plate may contact and cover the area of interest to provide a flatter, more even contour. The plate also diminishes tissue movement. Fluctuations in illumination can be compensated for by using image processing algorithms, including placing a constant shade gray image marker point at the area of interest as a control point.

The apparatus also comprises an optical detector for acquiring a signal representative of one or more optical properties of the area of interest. Any photon detector may be employed as an optical detector. Specialized detectors suited for detecting selected optical properties may be employed. One preferred optical detector for acquiring data in the format of an analog video signal is a charge coupled device (CCD) video camera which produces an output video signal at 30 Hz having, for example, 512 horizontal lines per frame using standard RS 170 convention. One suitable device is a CCD-72 Solid State Camera (Dage-MTI Inc., Michigan City, Ind.). Another suitable device is a COHU 6510 CCD Monochrome Camera with a COHU 6500 electronic control box (COHU Electronics, San Diego, Calif.). In some cameras, the analog signal is digitized 8-bits deep on an ADI board (analog-to-digital board). The CCD may be cooled, if necessary, to reduce thermal noise.

The optical imaging methods of the present invention may also usefully employ non-continuous illumination and detection techniques. For example, short pulse (time domain), pulsed time, and amplitude modulated (frequency domain) illumination sources may be used in conjunction with suitable detectors (See, Yodh, A., and Chance, B. *Physics Today*, March, 1995). Frequency domain illumination sources typically comprise an array of multiple source elements, such as laser diodes, with each element modulated at 180° out of phase with respect to adjacent elements (see, Chance, B. et al., (1993) *Proc. Natl. Acad. Sci. USA*, 90, 3423–3427). Two-dimensional arrays, comprising four or more elements in two orthogonal planes, can be employed to obtain two-dimensional localization information. Such techniques are described in U.S. Pat. Nos. 4,972,331 and 5,187,672 which are hereby incorporated by reference.

Time-of-flight and absorbance techniques (Benaron, D. A. and Stevenson, D. K. (1993) *Science*, 259, 1463–1466) may also be usefully employed in the present invention. In yet another embodiment of the present invention, a scanning laser beam may be used in conjunction with a suitable detector, such as a photomultiplier tube, to obtain high resolution images of an area of interest.

Image (data) processing is an important feature of the optical imaging techniques and apparatus of the present invention. In use, for example, CCD apparatus is preferably adjusted (at the level of the analog signal and before digitizing) to amplify the signal and spread the signal across the full possible dynamic range, thereby maximizing the sensitivity of the apparatus. Specific methods for detecting optical signals with sensitivity across a full dynamic range are described in detail in the patents incorporated herein by reference. Means for performing a histogram stretch of the difference frames (e.g., Histogram/Feature Extractor HF 151-1-V module, Imaging Technology, Woburn, Mass.) may be provided, for example, to enhance each difference image across its dynamic range. Exemplary linear histogram stretches are described in Green, *Digital Image Processing: A Systems Approach*, Van Nostrand Reinhold, N.Y., 1983. A histogram stretch takes the brightest pixel, or one with the highest value in the comparison image, and assigns it the maximum value. The lowest pixel value is assigned the minimum value, and every other value in between is assigned a linear value (for a linear histogram stretch) or a logarithmic value (for a log histogram stretch) between the maximum and minimum values. This allows the comparison image to take advantage of the full dynamic range and provide a high contrast image that clearly identifies areas of neuronal activity or inactivity.

Noise (such as 60 Hz noise from A.C. power lines) is filtered out in the control box by an analog filter. Additional adjustments may further enhance, amplify and condition the analog signal from a CCD detector. One means for adjusting the input analog signal is to digitize this signal at video speed (30 Hz), and view the area of interest as a digitized image that is subsequently converted back to analog format.

It is important that data, such as consecutive images of a particular area of interest, be aligned so that data corresponding to the same spatial location can be compared. If an averaged control image and a subsequent image are misaligned prior to comparison, artifacts will be present and the resulting comparison image will be more like a gradient image that amplifies noise and edge information. Image misalignment can be caused by patient motion, heartbeat and respiration. Large patient movements may require a new orientation of the camera and acquisition of a new averaged control image. It is possible, however, to compensate for small tissue movements by either mechanical or computational means, or a combination of both.

One way to relative movement of the optical detector and the area of interest is to rigidly secure the optical detector, and possibly the emr source, to the skeletal frame of the patient, such as by posts mounted on the cranium. The optical detector and emr source may also be provided as an integral limit to reduce relative motion. Other means for monitoring the optical detector and the illumination source in a constant orientation with respect to the area of interest may also be employed.

Real-time motion compensation and geometric transformations may also be used to align corresponding data. Simple mechanical translation of data or more complex (and generally more accurate) geometric transformation techniques can be implemented, depending upon the input data collection rate and amount and type of data processing. For many types of images, it is possible to compensate by a geometrical compensation which transforms the image by translation in the x-y plane. In order for an algorithm such as this to be feasible, it must be computationally efficient (preferably implementable in integer arithmetic), memory efficient, and robust with respect to changes in ambient light.

For example, functional control points can be placed in the area of interest and triangulation-type algorithms used to compensate for movements of these control points. Control points can be placed directly in the area of interest, such as directly on the cortical surface. Goshtasby ("Piecewise Linear Mapping Functions for Image Registration" in *Pattern Recognition* vol. 19 pp 459–66, 1986) describes a method whereby an image is divided into triangular regions using control points. A separate geometrical transformation is applied to each triangular region to spatially register each control point to a corresponding triangular region in a control image.

"Image warping" techniques may be employed whereby each subsequent image is registered geometrically to the averaged control image to compensate for movement. Image warping techniques described in, for example, Wolberg, "Digital Image Warping" IEEE Computer Society Press, Los Alimitos, Calif. 1990, may be used. Image warping techniques can further indicate when movement has become too great for effective compensation and a new averaged control image must be acquired.

The data processing function is generally operated and controlled by a host computer. The host computer may comprise any general computer (such as an IBM PC type with an Intel 386, 486 Pentium or similar microprocessor or Sun SPARC) that is interfaced with the emr source and/or optical detector directs data flow, computations, image acquisition and the like. Thus, the host computer controls acquisition and processing of data and provides a user interface.

According to a preferred embodiment, the host computer comprises a single-board embedded computer with a VME64 interface, or a standard (IEEE 1014–1987) VME interface, depending upon bus band width considerations. Host computer boards which may be employed in the present invention include, for example, Force SPARC/CPU-2E and HP9000 Model 7471. The user interface can be, for example, a Unix/X-Window environment. The image processing board can be, for example, based upon Texas Instruments' MVP and other chips to provide real-time image averaging, registration and other processing necessary to produce high quality difference images for intraoperative viewing. This board will also drive a 120×1024 RGB display to show a sequence of difference images over time with pseudo-color mapping to highlight tumor tissue. Preferably, a second monitor is used for the host computer to increase the overall screen real estate and smooth the user interface. The processing board (fully programmable) can support a VME64 master interface to control data transactions with the other boards. Lastly, a peripheral control board can provide electrical interfaces to control mechanical interfaces from the host computer. Such mechanical interfaces can include, for example, the light source and optical detector control box.

A real-time data acquisition and display system, for example, may comprise four boards for acquisition, image processing, peripheral control and host computer. A minimal configuration with reduced processing capabilities may comprise just the acquisition and host computer boards. The acquisition board comprises circuitry to perform real-time averaging of incoming video frames and allow readout of averaged frames at a maximum rate bus. A VME bus is preferred because of its high peak bandwidth and compatibility with a multitude of existing VME products. The acquisition board should also support many different types of optical detectors via a variable scan interface. A daughter board may support the interfacing needs of many different types of optical detectors and supply variable scan signals to the acquisition motherboard. Preferably, the unit comprises a daughter board interfacing to an RS-170A video signal to support a wide base of cameras. Other camera types, such as slow scan cameras with a higher spatial/contrast resolution and/or better signal to noise ratio, can be developed and incorporated in the inventive device, as well as improved daughter boards to accommodate such improved cameras.

According to a preferred embodiment, data, such as analog video signals, are continuously processed using, for example, an image analyzer (e.g., Series 151 Image Processor, Imaging Technologies, Inc. Woburn, Mass.). An image analyzer can receive and digitize an analog video signal with an analog to digital interface and perform such a function at a frame speed of about $\frac{1}{30}$th of a second (e.g., 30 Hz or "video speed"). Processing the signal involves first digitizing the signal into a series of pixels or small squares assigned a value (in a binary system) dependent upon the number of photons (i.e., quantity of emr) being reflected off tissue from the part of the area of interest assigned to that pixel. For example, in a standard 512×512 image from a CCD camera, there would be 262,144 pixels per image. In an 8 bit system, each pixel is represented by 8 bits corresponding to one of 256 levels of gray.

The signal processing means preferably includes a programmable look-up table (e.g., CM150-LUT16, Imaging Technology, Woburn, Mass.) initialized with values for converting gray coded pixel values, representative of a black and white image, to color coded values based upon the intensity of each gray coded value. This can provide image enhancement via an image stretch. An image stretch is a technique whereby the highest and lowest pixel intensity values used to represent each of the pixels in a digital image frame are determined over a region of the image frame which is to be stretched. Stretching a selected region over a larger range of values permits, for example, easier identification and removal of relatively high, spurious values due to noise (e.g., glare).

The processing means may further include a plurality of frame buffers having frame storage areas for storing frames of digitized image data received from the A/D interface. The frame storage area comprises at least one megabyte of memory space, and preferably at least 8 megabytes of storage space. An additional 16-bit frame storage area is preferred as an accumulator for storing processed image frames having pixel intensities represented by more than 8 bits. The processing means preferably includes at least three frame buffers, one for storing the averaged control image, another for storing the subsequent image, and a third for storing a comparison image.

According to preferred embodiments, the processing means further comprises an arithmetic logic unit (e.g, ALU-150 Pipeline Processor) for performing arithmetical and logical functions on data located in one or more frame buffers. An ALU may, for example, provide image (data) averaging in real time. A newly acquired digitized image may be sent directly to the ALU and combined with control image stored in a frame buffer. A 16 bit result can be processed through an ALU, which will divide this result by a constant (i.e., the total number of images). The output from the ALU may be stored in a frame buffer, further processed, or used as an input and combined with another image.

Normally, areas of increased neuronal activity exhibit an increase of the emr absorption capacity of neuronal tissue (i.e., the tissue gets darker if visible light is used for emr illumination, or an intrinsic signal increases in a positive direction). Similarly, a decrease in neuronal activity is indicated a decrease of emr absorption capacity of the tissue (i.e., the tissue appears brighter, or intrinsic signals become negative). For example, image A is a subsequent averaged image and image B is an averaged control image. Normally, when a pixel in image A is subtracted from a pixel in image B and a negative value results, this value is treated as zero. Hence, difference images cannot account for areas of inhibition. The present invention provides a method for identifying both negative and positive intrinsic signals, by: (a) subtracting image A (a subsequent averaged image) from image B (an averaged control image) to create a first difference image, whereby all negative pixel values are zero; and (b) subtracting image B from image A to create a second difference image whereby all negative pixel values are zero; and adding the first and second difference images to create a "sum difference image." The sum difference image shows areas of increased activity (i.e., color coded with warmer colors such as yellow, orange, red) and show areas of less activity or inhibition (i.e., color coded with colder colors such as green, blue, purple). Alternatively, one can overlay the first difference image on the second difference image. Either method provides an image of increased neuronal activity and decreased neuronal activity. The difference output may be superimposed upon the real time analog video image to provide a video image of the area of interest (e.g., cortical surface) superimposed with a color-coded difference frame, in frozen time, to indicate where there are intrinsic signals in response to some stimulus or paradigm.

The comparison (e.g., difference) data is, preferably, further processed to smooth out the image and remove high frequency noise. For example, a lowpass spatial filter can block high spatial frequencies and/or low spatial frequencies to remove high frequency noises at either end of the dynamic range. This provides a smoothed-out processed difference image (in digital format). The digitally processed difference image can be color-coded by assigning a spectrum of colors to differing shades of gray. This image is then converted back to an analog image (by an ADI board) and displayed for a real time visualization of differences between an averaged control image and subsequent images. Moreover, the processed difference image can be superimposed over the analog image to display specific tissue sites where a contrast enhancing agent may have a faster uptake, or where an intrinsic signal may be occurring.

Processing speed may be enhanced by adding a real time modular processor or faster CPU chip to the image processor. One example of a real time modular processor which may be employed in the present invention is a 150 RTMP-150 Real Time Modular Processor (Imaging Technology, Woburn, Mass.).

The processing means may further include an optical disk for storing digital data, a printer for providing a hard copy of the digital and/or analog data and a display, such as a video monitor to permit the physician to continuously monitor the comparison data output.

A single chassis may house all of the modules necessary to provide optical imaging according to the present invention. The necessary components, whether or to whatever degree integrated, may be installed on a rack that is easily transportable within and between operating and hospital rooms along with display monitors and peripheral input and output devices.

Imaging Methods

Methods for imaging neuronal activity involve comparison of control data to data acquired during neuronal activity, inhibition or dysfunction. Neuronal tissue may be stimulated or inhibited without applying any external influence. Seizures, strokes, neuronal dysfunction and tissue non-viability are exemplary of such occurrences. Alternatively, intrinsic signals may be evoked by stimulating neuronal tissue using direct stimulation techniques or specific paradigms. Suitable paradigms are well known in the art and include, for example, presenting pictures of objects to a patient and asking the patient to name the object. Such naming exercises alter neuronal activity and produce an associated intrinsic signal.

An optical detector, such as a video CCD, is focused upon the area of interest during high intensity emr illumination. A first averaged image may be acquired, digitized and stored in a frame buffer. During an imaging study, it is important to update the averaged image frame frequently to account for patient movement and for tissue movements due to surgical manipulation. The area of interest is subsequently monitored at regular intervals, or an appropriate paradigm is administered. Subsequent image frames are acquired and stored, and subtractively compared to produce difference images (preferably, one or two per second) using the above-described processing means. The areas in which neuronal activity has occurred are indicated in the difference image. The difference image can be stored to allow the surgeon to study the area of interest in real time during an operation.

The present invention further provides a method for imaging of cortical functional areas and dysfunctional areas, such as those areas of severe epileptic activity. The method involves administering a paradigm to evoke an intrinsic signal for mapping a particular cortical function, or identifying an area of hyperactivity that is the location of epileptic activity in an epileptic patient. An epileptogenic area of the cortex is visualized as spontaneously more active and can be imaged by the inventive apparatus by mapping intrinsic signals of cortical activity. Retinal function and dysfunction may also be detected and monitored using the optical imaging techniques described herein.

The inventive apparatus and method may also be employed to image peripheral nerve damage and scarring. Nerves of the central and peripheral nervous system (PNS) are characterized by the ability to regenerate after damage. During operations to repair damaged peripheral or cranial nerves, one can image areas of nerve damage by imaging areas of blockage of intrinsic signals. For example, the nerve is exposed in the area of interest and then stimulated upstream of the site of damage. The active nerve pathway is imaged by intrinsic signals in the processed difference image after stimulation. The site of nerve damage or blockage is evidenced by an abrupt end or diminution to the intrinsic signal. In this way, the surgeon is able to obtain real time information on the precise location of nerve damage and to correct the damage, if possible.

The imaging method may acquire data at the surface of an area of interest. As described above, longer wavelengths of emr (in the infrared range) can be used to image areas of interest which are deeper in tissue or below overlying tissue. In some areas of the body longer wavelength visible light and near infrared emr can easily pass through such tissue for imaging. Moreover, if a difference image is created between the image acquired at 500 nm emr and the image acquired at 700 nm emr, the difference image will show an optical slice of tissue. Administration of an imaging agent which absorbs specific wavelengths of emr can act as a tissue filter of emr to provide a filter in the area of interest. In this instance, it is desirable to utilize an imaging agent that remains in the tissue for a prolonged period of time.

EXAMPLE 1

This example illustrates optical changes indicative of neuronal activity in a human subject by direct cortical electrical stimulation. Surface electrical recordings (surface EEG, ECOG) were correlated with optical changes. Intrinsic optical changes were evoked in an awake patient during stimulating-electrode "calibration". Four stimulation trials were sequentially applied to the cortical surface, each stimulation evoking an epileptiform afterdischarge episode. A stimulation trial consisted of: 1) monitoring resting cortical activity by observing the output of the recording electrodes for a brief period of time, 2) applying an electric current via the stimulation-electrodes to the cortical surface at a particular current for several seconds, and 3) monitoring the output of the recording electrodes for a period of time after stimulation has ceased.

The cortex was evenly illuminated by a fiber optic emr passing through a beam splitter, controlled by a D.C. regulated power supply (Lambda, Inc.) and passed through a 695 nm longpass filter. Images were acquired with a CCD camera (COHU 6500) fitted to the operating microscope with a specially modified cineadaptor. The cortex was stabilized with a glass footplate. Images were acquired at 30 Hz and digitized at 8 bits (512×480 pixels, using an Imaging Technology Inc. Series 151 system, Woburn, Mass.). Geometric transformations were applied to images to compensate for small amounts of patient motion (Wohlberg, *Digital Imaging Warping*, I.E.E.E. Computer Society, Los Alamitos, Calif., 1988). Subtraction of images collected during the stimulated state (e.g., during cortical surface stimulation, tongue movement or naming) from those collected during a control state with subsequent division by a control image resulted in percentage difference maps. Raw data (i.e., no digital enhancement) were used for determining the average optical change in specified regions (average sized boxes was 30×30 pixels or 150–250 $\mu m^2$). For pseudocolor images, a linear low pass filter removed high frequency noise and linear histogram transformations were applied. Noise was defined as the standard deviation of fluctuations in sequentially acquired control images as 0.003–0.009.

A series of images (each image consisting of an average of 128 frames acquired at 30 Hz) were acquired during each of the four stimulation trials. A current of 6 mA was used for the first three stimulation trials, and 8 mA for the fourth. After a sequence of 3–6 averaged control images were acquired, a bipolar cortical stimulation current was applied (either 6 mA or 8 mA) until epileptiform after discharge activity was evoked (as recorded by the surface electrode). Images were continuously acquired throughout each of the four stimulation trials.

The percentage change in absorption of light for each pixel was calculated for each image acquired during the four stimulation trials. The average percentage changes over the four areas (indicated by the four square regions marked in FIG. 1A) were plotted graphically in FIGS. 1B, 1C, and 1D for comparison and analysis of the dynamic changes occurring in these four spatial areas.

Figure 1B:
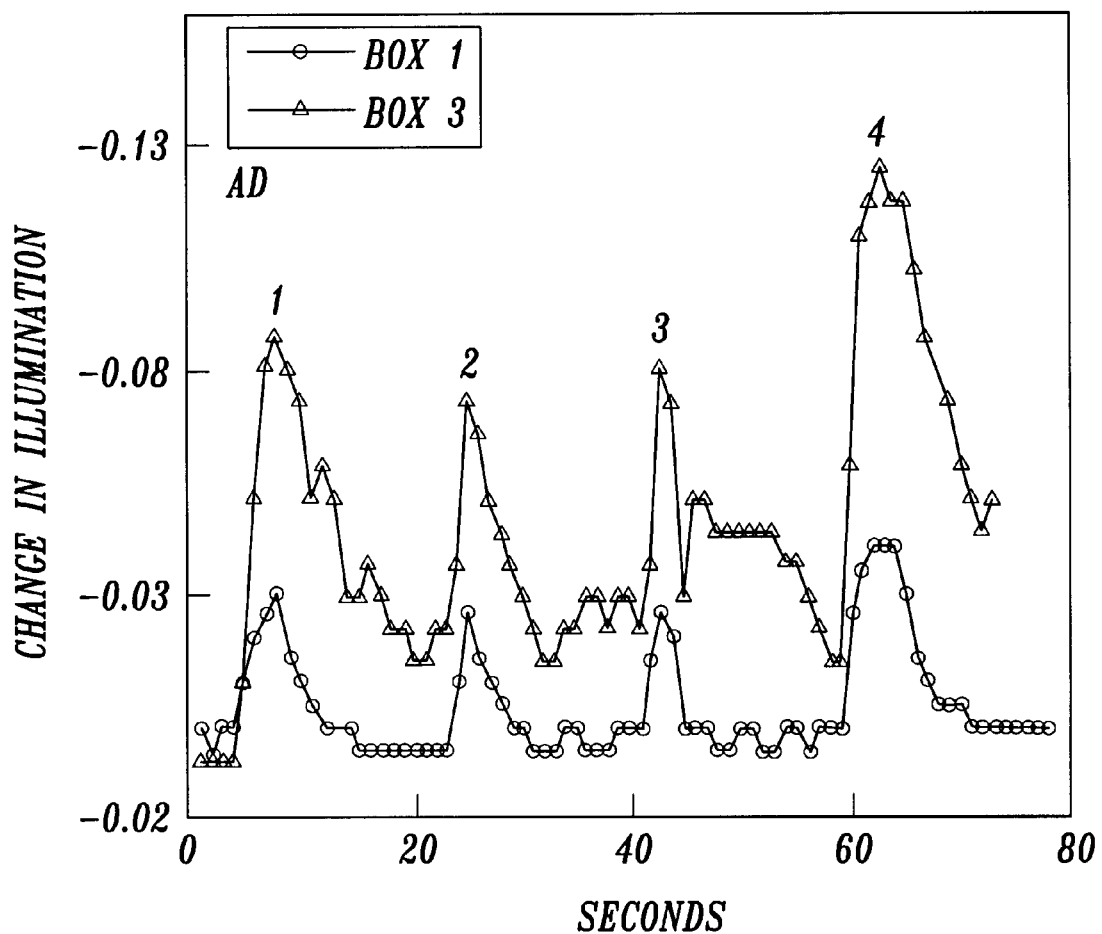
FIG. 1B shows plots of the percent optical change per second in the spatial regions of boxes 1 and 3 (as labeled in FIG. 1A). For both regions, the peak change is during the fourth stimulation trial (at 8 mA), in which the greatest amount of stimulating current had induced the most prolonged epileptiform afterdischarge activity. The changes within box 3 were greater and more prolonged than those of box 1. Box 3 was overlying the area of the epileptic focus.
Figure 1C:
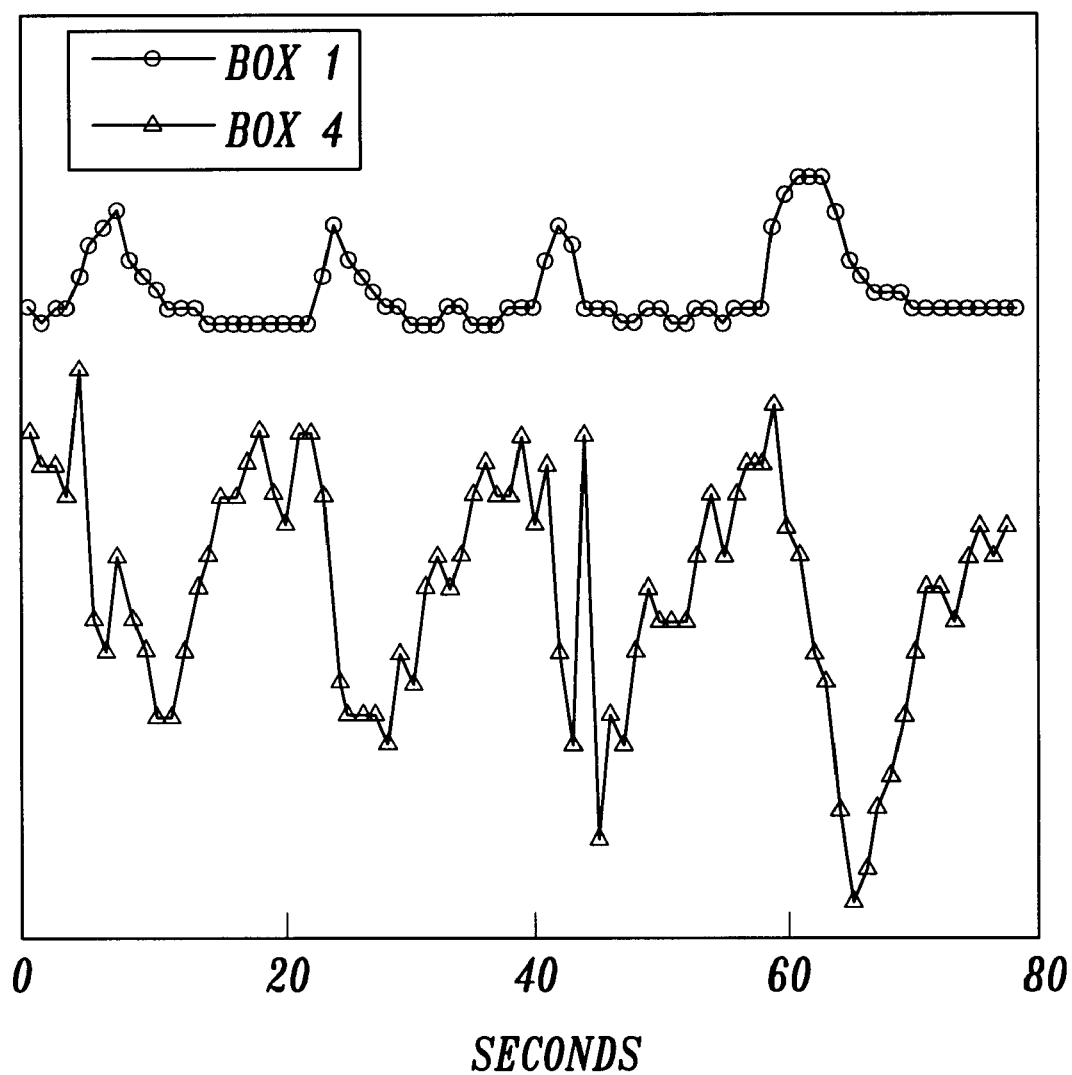
FIG. 1C show plots of the percent optical change per second in the spatial regions of boxes 1 and 4 (as labeled in FIG. 1A). Box 1 overlays and area of cortical tissue between the two stimulating electrodes, and box 4 overlays a blood vessel. The optical changes within box 4 are much larger and in the opposite direction of box 1. Also, these changes are graded with the magnitude of stimulating current and afterdischarge activity. The changes in box 4 are most likely due to changes of the blood-flow rate within a blood vessel. This data demonstrates that the methods and apparatus of the present invention can be used to simultaneously monitor cortical activity and blood-flow.
Figure 1D:
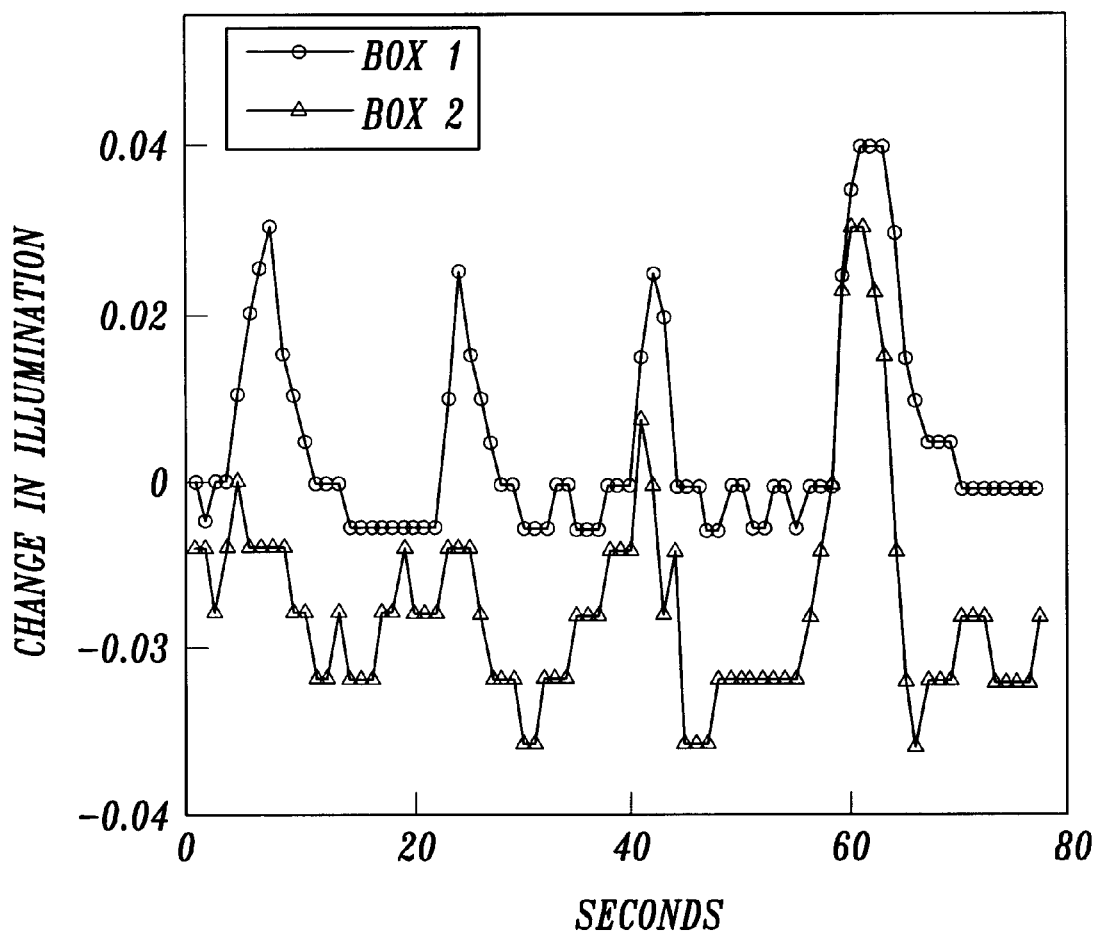
FIG. 1D shows plots of the percent optical change absorption per second in the spatial regions of boxes 1 and 2 (as labeled in FIG. 1A). Note that although these two areas are nearby each other, their optical changes are in the opposite direction during the first three stimulation trials using 6 mA current. The negative going changes within the region of box 2 indicate that the methods and apparatus of the present invention may be used to monitor inhibition of cortical activity as well as excitation.
Figure 3A:
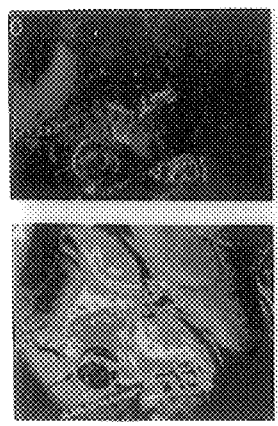
FIG. 3 shows eight percentage difference images from stimulation trial 2 described in the previous two Figures. Each image is integrated over a two second interval. The focal area of greatest optical change is in the center of images 3C, 3D, and 3E, indicating the region of greatest cortical activity. This region is the epileptic focus. The magnitude of optical change is indicated by the gray-scale bar on the right side of the Figure. The arrow beside this gray-scale indicates the direction of increasing amplitude. Each image maps an area of cortex approximately 4 cm by 4 cm.
Figure 3B:
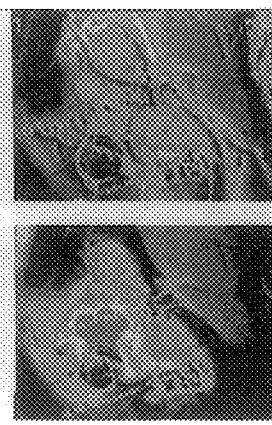
Figure 3C:
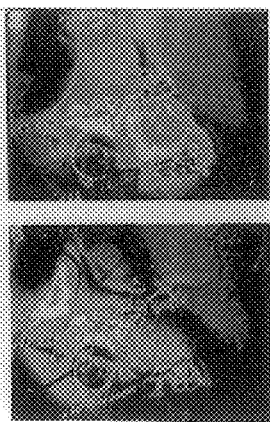
Figure 3D:
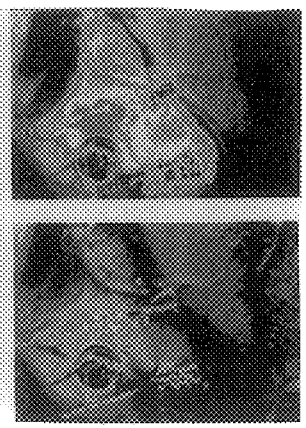
Figure 3E:
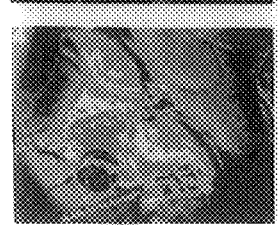
Figure 3F:
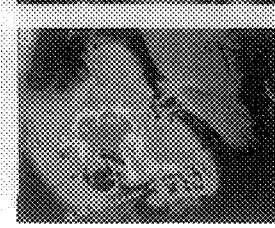
Figure 3G:
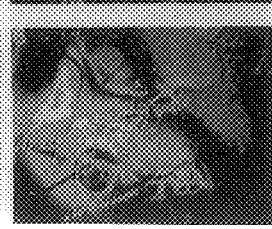
Figure 3H:
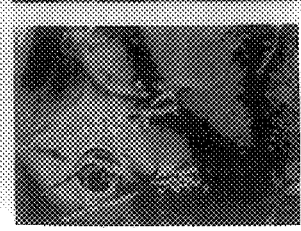

The optical changes between the stimulating electrodes (site #1, FIG. 1A) and near the recording electrode (site #3) showed a graded response to the intensity and duration of each afterdischarge episode (FIG. 1B). The spatial extent of the epileptiform activity was demonstrated by comparing a baseline image collected before stimulation to those obtained immediately after stimulation. The intensity and spread of the optical changes were much less following stimulation #2 (shortest least intense afterdischarge episode) than after stimulation #4 (longest most intense afterdischarge episode).

When the optical changes were below baseline, the surface EEG recordings did not identify epileptiform activity (n=3 patients). At site #3 in FIG. 2A1, the optical changes after stimulation were below baseline (i.e., black regions in FIG. 2A3). However, during the fourth stimulation, the epileptiform activity spread into the area of site #3 and the optical signal did not go below baseline until later (site #3, FIG. 1B). This negative optical signal likely represents inhibited neuronal populations (an epileptic inhibitory surround), decreased oxygen delivery, or blood volume shunted to activated regions. The data illustrated in FIGS. 1–4 also corresponds to Example 1.

EXAMPLE 2

Figure 7A:
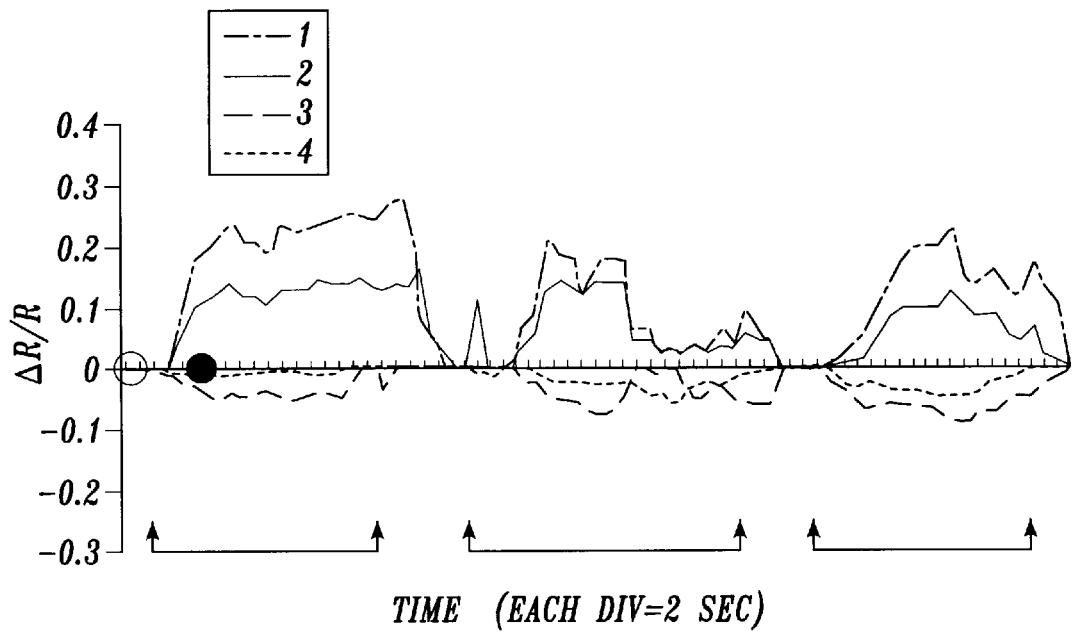
FIG. 7A shows the plots during the three tongue wiggling trials averaged spatially within the boxes 1, 2, 3, and 4 as identified in FIG. 6A1.
Figure 7B:
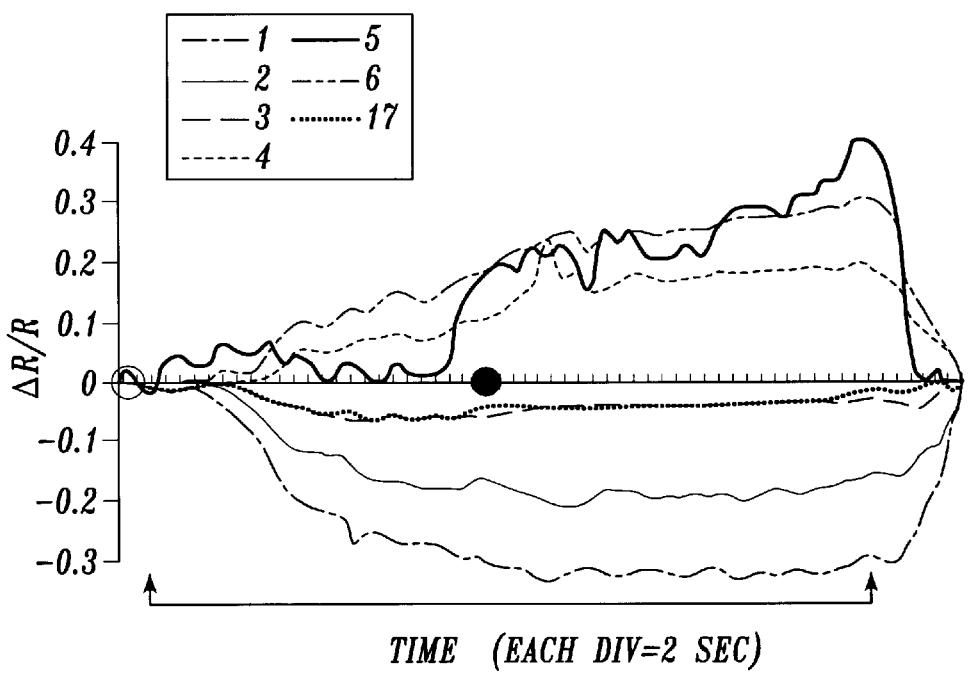
FIG. 7B shows the plots during one of the language naming trials averaged spatially within the boxes 1–7 and 17.

Stimulation mapping of the cortical surface was performed on awake human patients under local anesthesia to identify sensory/motor cortex and Broca's areas. The illumination source and optical detection device and processing techniques used were the same as those described in Example 1. During three "tongue wiggling" trials, images were averaged (32 frames, 1 sec) and stored every 2 seconds. A tongue wiggling trial consisted of acquiring 5–6 images during rest, then acquiring images during the 40 seconds that the patient was required to wiggle his tongue against the roof of his mouth, and then to continue acquiring images during a recovery period. The same patient was then required to engage in a "language naming" trial. A language naming trial consisted of acquiring 5–8 images during rest (control images—the patient silently viewing a series of blank slides), then acquiring images during the period of time that the patient engaged in the naming paradigm (naming a series of objects presented with a slide projector every 2 seconds, selected to evoke a large response in Broca's area), and finally a series of images during the recovery period following the time when the patient ceased his naming task (again viewing blank slides while remaining silent). The results are shown in FIGS. 6 and 7 and described in the description of those Figures These results agree with those data reported by Lee et al. (*Ann. Neurol.* 20:32, 1986), who reported large electrical potentials in the sensory cortex during finger movement. The magnitude of the optical changes in the sensory cortex during tongue movement (10–30%) parallels sensory/motor cortex studies where cerebral blood flow increases 10–30% during motor tasks (Colebatch et al., *J. Neurophysiol.* 65:1392, 1991). Further, utilizing Magnetic Resonance Imaging (MRI) of blood volume changes in human visual cortex during visual stimulation, investigators have demonstrated increases of up to 30% in cerebral blood volume (Belliveau et al., *Science* 254:716, 1991).

Optical images were obtained from this same cortical region (i.e., area of interest) while the patient viewed blank slides and while naming objects on slides presented every two seconds. Percentage difference maps obtained during naming showed activation of the premotor area. The sites of speech arrest and palate tingling were identified by surface stimulation and demonstrate optical signals going in the opposite direction. The area of activation was clearly different from that evoked by tongue movement without speech production. The optical images of premotor cortex activation during naming were in similar locations to the cortical areas identified in PET single word processing studies (Peterson, et al., *Nature* 331:585, 1991; and Frith et al., *J. Neuropsychologia* 29:1137, 1991). The optical changes were greatest in the area of the cortex traditionally defined as Broca's area and not in areas where electrical stimulation caused speech arrest.

EXAMPLE 3

Figure 9A:
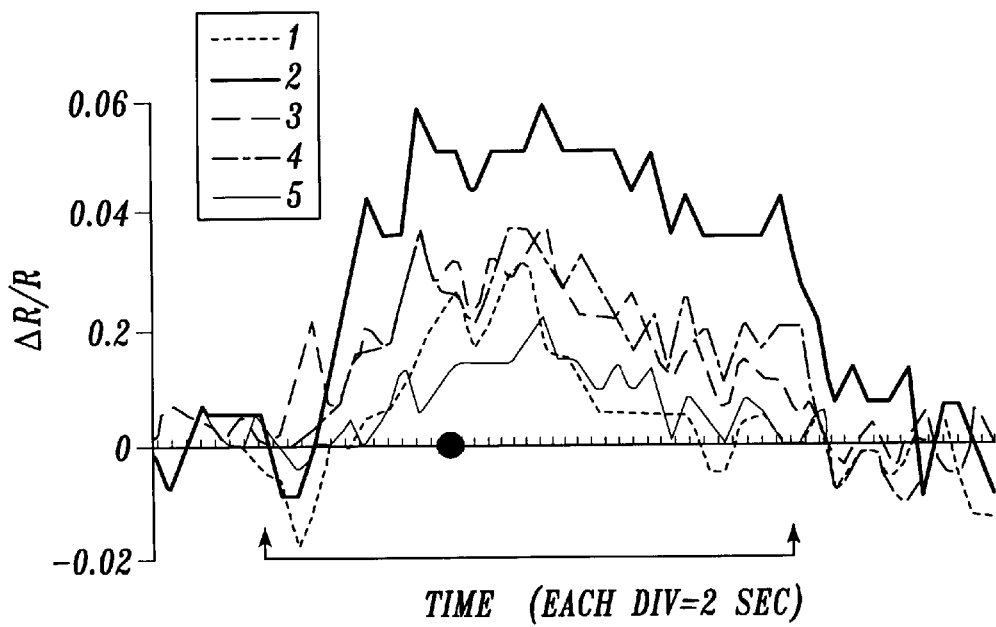
FIG. 9A shows plots of percentage change in optical absorption of tissue within the boxed regions shown in FIG. 8. The plots of boxes 1 and 2 overlay essential language sites, and boxes labeled 4, 5, and 6 overlay secondary language sites. Each of these five sights showed significant changes occurring while the patient was engaged in a language naming task.
Figure 9B:
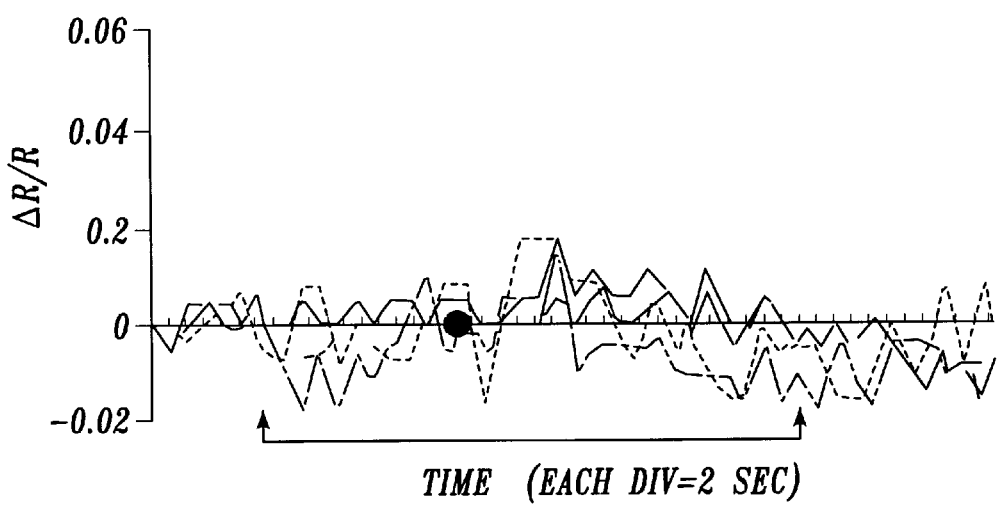
FIG. 9B shows percentage changes from the six unlabeled boxes shown in FIG. 8. There were no significant increases or decreases within these anterior sites.
Figure 10A:
FIG. 10A is a gray-scale image of the cranial surface of a rat. The sagittal suture runs down the center of the image. Box 1 lays over the suspected region of brain tumor, and box 2 lays over normal tissue.
Figure 10B:
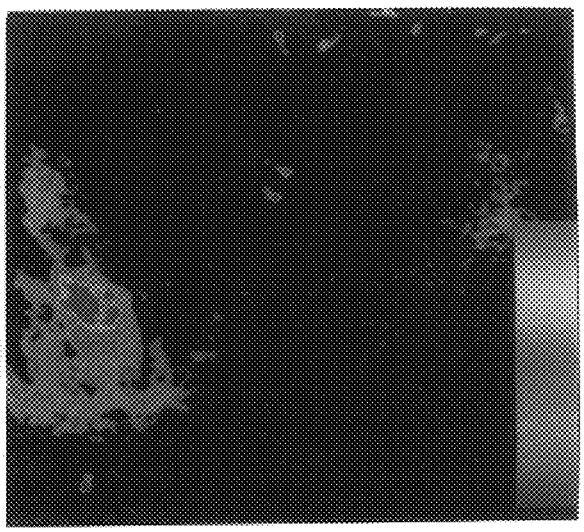
FIG. 10B is a difference image 1 second after indocyanine green dye had been intravenously injected into the animal. The region containing tumor tissue became immediately visible through the intact cranium.
Figure 10C:
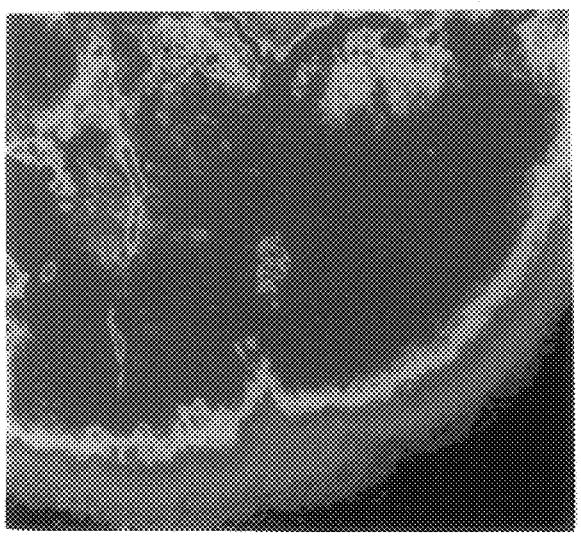
FIG. 10C shows that 5 seconds after dye injection the dye can be seen to profuse through both normal and tumor tissue.
Figure 10D:
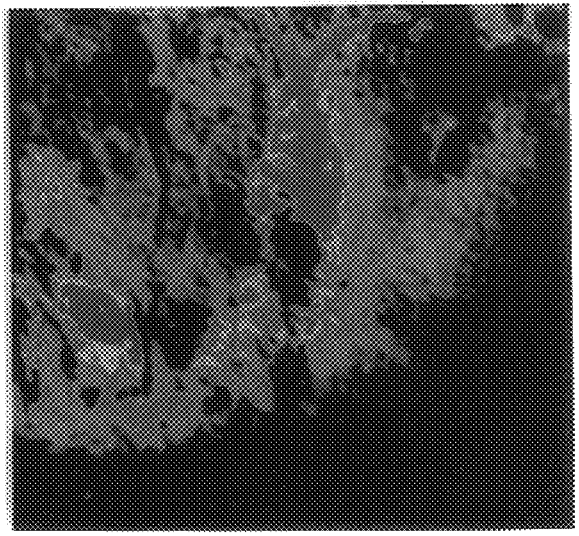
Figure 11A:
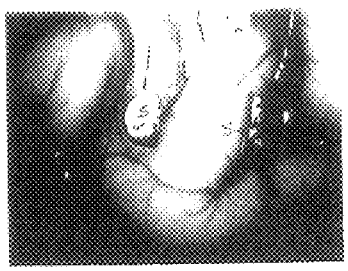
FIG. 11A is a grey-scale image of a human cortex just anterior to face-motor cortex with two stimulating electrodes (s).
Figure 11B:
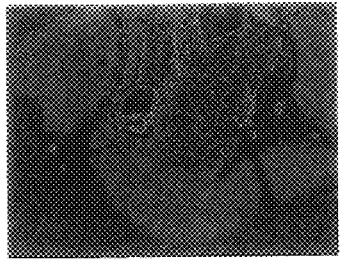
FIG. 11B is spatial map of baseline cortical activity prior to application of stimulating current for inducing epileptiform afterdischarge activity.
Figure 11C:
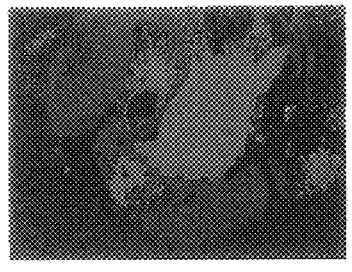
FIG. 11C is a spatial map of cortical activity during stimulation at stimulating electrodes (s) and the resulting epileptiform afterdischarge activity.
Figure 11D:
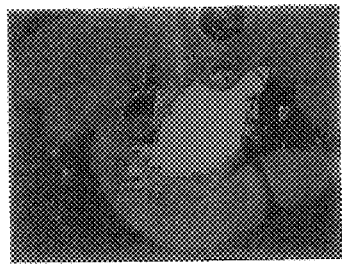
FIG. 11D is a spatial map of cortical activity during an apparent quiescent period following the epileptiform afterdischarge activity induced by stimulation at stimulating electrodes (s).
Figure 11E:
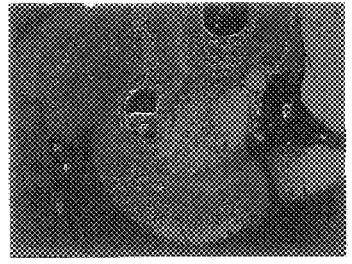
FIG. 11E is a spatial map of cortical activity of a period following the quiescent period represented by FIG. 11D.
Figure 12:
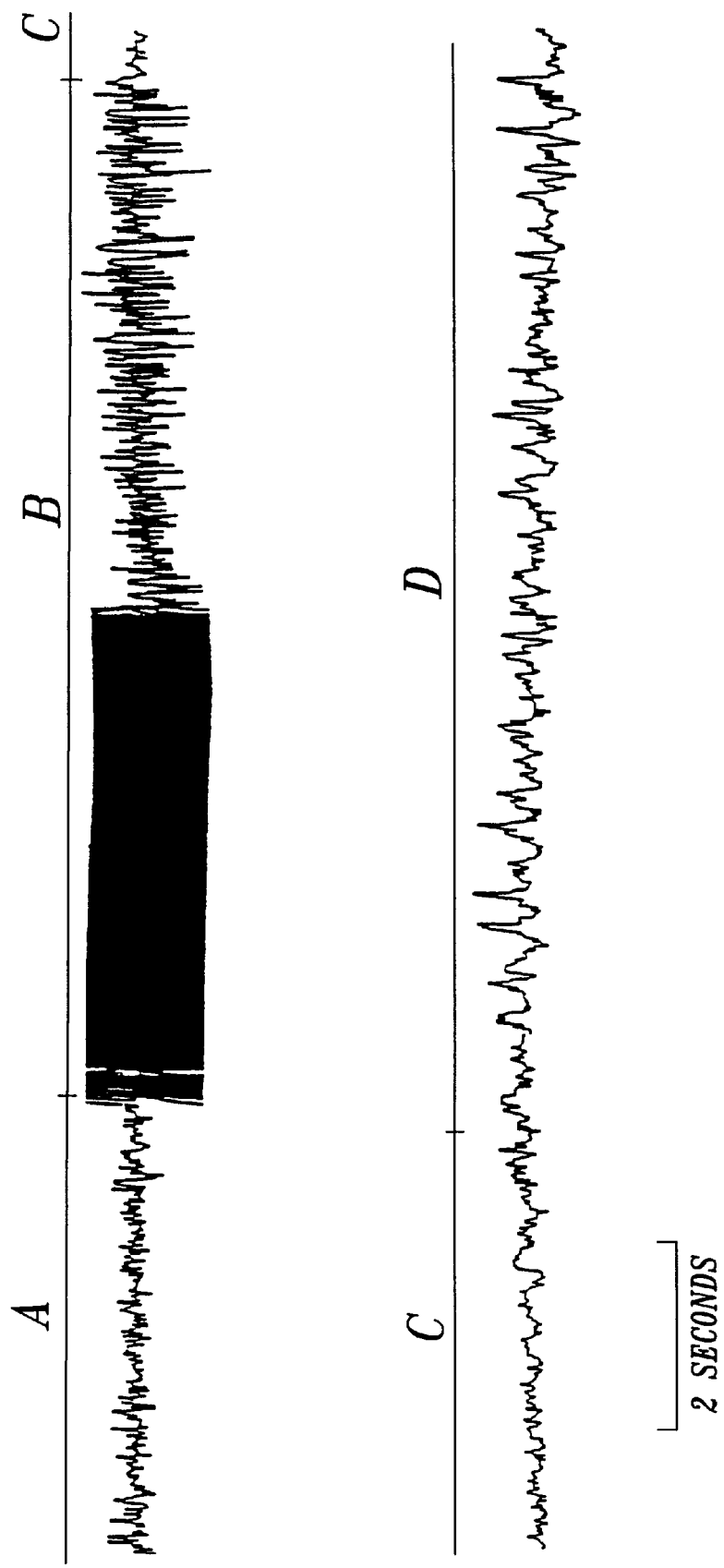
FIG. 12 is a trace of an EEG recording of surface electrical signals received by recording electrode (r) shown in FIG. 11A and corresponding to the baseline cortical activity of FIG. 11B (period A), the cortical activity during stimulation and the resulting epileptiform afterdischarge activity of FIG. 11C (period B), the quiescent cortical activity following the epileptiform afterdischarge activity of FIG. 11D (period C), and the subsequent cortical activity of FIG. 11E (period D).

Human cortex was imaged using the illumination source and optical detector described in Example 1. Functional mapping was conducted prior to and during imaging, as described with reference to FIGS. 8 and 9. The data illustrated in FIG. 8 demonstrates how a surgeon might use this invention intraoperatively to map language cortex and to avoid surgically removing tissue having important functional properties. The data illustrated in FIG. 9 demonstrate that optical imaging can also identify both essential and secondary language areas that must be preserved during neurosurgical procedures.

EXAMPLE 4

Figure 5A:
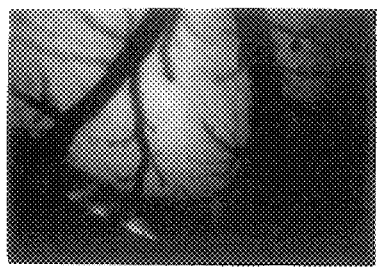
FIG. 5A, is a gray-scale image of hind limb somatosensory cortex in an anesthetized rat. The magnification is sufficiently high so that individual capillaries can be distinguished (the smallest vessels visible in this image). The center image.
Figure 5B:
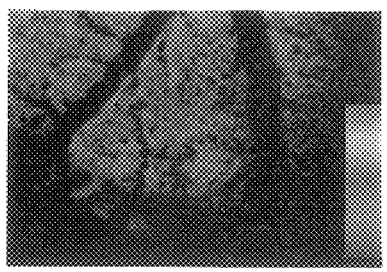
FIG. 5B, is an image of a percentage difference control optical image during rest. The magnitude of optical change is indicated by the gray-scale bar on the right side of this image. The rightmost image.
Figure 5C:
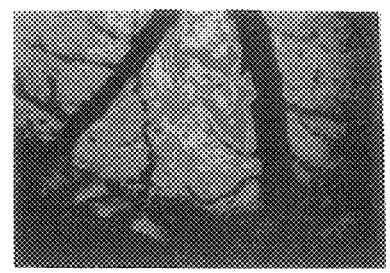
FIG. 5C, is a percentage difference map of the optical changes in the hind limb somatosensory cortex during stimulation of the sciatic nerve.

Activation of sensory cortex by stimulation of a peripheral nerve was imaged using a rat model. The results are shown in and described with reference to FIG. 5. This data demonstrates that the method and apparatus of the present invention may be used to map functional areas of the cortex providing afferent input while the subject is anesthetized.

EXAMPLE 5

Areas of interest can be imaged through intact tissues, such as bone, dura, muscle, connective tissue and the like. FIG. 10 illustrates identification of a brain tumor through the intact cranium using optical imaging techniques of the present invention. Tumor cells were injected into the left side of the intact cranium of a rat to cause development of a glioma on the left brain hemisphere. The right hemisphere was normal. FIGS. 10A–10D illustrate the dynamics and visibility of dye perfusion in both the tumor and neuronal tissue. Neuronal activity may likewise be imaged "through" intact tissues.

EXAMPLE 6

Optical contrast enhancing agents may be used in connection with optical imaging techniques of the present invention. The utility of such agents may be demonstrated using hippocampal brain slice preparations. Hippocampal slices may be loaded in a chamber provided with artificial cerebral spinal fluid ("ACSF"), albumin labelled with indocyanine green ("ICG") (approx. 2 mM) and 2% DMSO. After one hour, the tissue will be visibly stained. Because the albumin-labeled ICG collects in the extracellular space, this staining technique may be used to detect changes in neuronal activity and/or functions that are correlated to changes in the volumes of the extracellular space. Similarly, the fluorescent agent Biodipy (available from Molecular Probes, Inc., P.O. Box 22010, Eugene, Oreg. 97402) bound to albumin will collect in extracellular space and may be used as a contrast enhancing agent to detect neuronal states or changes correlated to changes in the volume of the extracellular space.

We claim:

1. A physiologically non-invasive method for detecting optical changes indicative of neuronal activity or dysfunction in an area of interest in a human patient, comprising:
   (a) illuminating the area of interest with an illumination source emitting electromagnetic radiation (emr) having at least one wavelength of from about 450 nm to about 2500 nm;
   (b) detecting one or more optical properties of the area of interest when it is illuminated with the emr using a photon detector and acquiring and storing a control data set representing the one or more optical properties detected;
   (c) detecting one or more properties of the area of interest at a time different from acquisition of the control data set and acquiring a subsequent data set representing the one or more optical properties detected during the different time; and
   (d) comparing the subsequent data set with the control data set to produce a comparison data set that identifies changes in the one or more optical properties and thereby identifies areas of neuronal activity or dysfunction.

2. A method according to claim 1, additionally comprising inducing neuronal activity in the area of interest by administering an electrical stimulus to neuronal tissue.

3. A method according to claim 1, additionally comprising inducing neuronal activity in the area of interest by administering a paradigm that stimulates intrinsic neuronal activity.

4. A method according to claim 1, wherein neuronal activity is induced by a natural occurrence.

5. A method according to claim 1, wherein the illumination source and the photon detector are fixed in position relative to one another.

6. A method according to claim 1, wherein the illumination source and the photon detector are fixed relative to one another and are mounted to the human patient.

7. A method according to claim 1, wherein the area of interest includes a peripheral nerve.

8. A method according to claim 1, wherein the area of interest comprises neuronal cortex.

9. A method according to claim 1, wherein the photon detector is a video camera.

10. A method according to claim 1, additionally comprising amplifying portions of the control data set to enhance a contrast of the comparison data set.

11. A method according to claim 1, additionally comprising identifying data points in the comparison data set having intermediate values that represent optical changes indicative of neuronal activity, and mapping the data points having intermediate values to one of logarithmically and linearly increasing values to enhance the contrast of the comparison data set.

12. A method according to claim 1, wherein the control data set is a control image, the subsequent data set is a subsequent image, and the comparison data set is a comparison image.

13. A method according to claim 1, additionally comprising aligning corresponding spatial locations in the control and subsequent data sets to produce the comparison data set.

14. A method according to claim 1, additionally comprising mapping different pixel values comprising a comparison image to color values to enhance a contrast of the comparison image.

15. A method according to claim 14, wherein positive-going optical changes are mapped to a first color value and negative-going optical signals are mapped to a second color value.

16. A method according to claim 1, comprising detecting one or more optical properties selected from the group consisting of: reflection; refraction; diffraction; absorption; scattering; birefringence; refractive index; and Kerr effect.

17. A method according to claim 1, comprising continuously illuminating the area of interest.

18. A method according to claim 1, comprising illuminating the area of interest non-continuously.

19. A method according to claim 18, comprising illuminating the area of interest using a short pulse (time domain), pulsed time, or amplitude modulated (frequency domain) illumination source.

20. A method according to claim 1, comprising illuminating the area of interest uniformly.

21. A method according to claim 1, comprising illuminating the area of interest with an illumination source emitting emr having at least one wavelength in the infrared range.

22. A method according to claim 1, performed intraoperatively.

23. A method for optically imaging changes indicative of changes in neuronal activity in an area of interest in a human patient, comprising:
   (a) illuminating an area of interest with an illumination source emitting electromagnetic radiation (emr) having a wavelength of from about 450 nm to about 2500 nm by connecting the illumination source to an illumination probe and implementing the illumination probe in the area of interest;
   (b) detecting one or more optical properties of the area of interest when it is illuminated with the emr using a photon detector connected to a detection probe implanted in the area of interest that produces detection signals;
   (c) conveying control detection signals to a data processor and producing a control data set representing the one or more optical properties detected;
   (d) detecting one or more optical properties of the area of interest during neuronal activity, producing subsequent detection signals, conveying the subsequent detection signals to the data processor, and producing a subsequent data set representing the one or more optical properties detected during neuronal activity; and (e) comparing the subsequent data set with the control data set to produce a comparison data set that identifies changes in one or more optical properties and thereby identifies areas of neuronal activity.

24. A method for identifying spatial locations corresponding to functional properties of neuronal tissue in a human patient comprising:

(a) illuminating neuronal tissue with an illumination source emitting electromagnetic radiation (emr) having one or more wavelengths of from about 450 nm to about 2500 nm;

(b) detecting one or more optical properties of identifiable spatial locations of the neuronal tissue when it is illuminated and acquiring a control image that maps the one or more detected optical properties to identifiable spatial locations of the neuronal tissue;

(c) detecting one or more optical properties of neuronal tissue during neuronal stimulation and acquiring a subsequent image that maps the one or more detected optical properties during neuronal stimulation to identifiable spatial locations of the neuronal tissue; and (d) comparing the control image to the subsequent image to produce a comparison image that spatially locates changes in neuronal activity.

25. A method according to claim 24, additionally comprising inducing neuronal activity in the neuronal tissue by administering a paradigm that stimulates intrinsic neuronal signals.

26. A physiologically non-invasive method for optically imaging changes indicative of changes in retinal function in a retina in a human patient, comprising:

(a) illuminating the retina with an illumination source emitting electromagnetic radiation (emr) having at least one wavelength of from about 450 nm to about 2500 nm;

(b) detecting one or more optical properties of the retina when it is illuminated with the emr using a photon detector and acquiring and storing a control data set representing the one or more optical properties detected;

(c) detecting one or more optical properties of the retina during retinal activity and acquiring a subsequent data set representing the one or more optical properties detected during retinal activity; and (d) comparing the subsequent data set with the control data set to produce a comparison data set that identifies changes in the one or more optical properties and thereby identifies areas of retinal dysfunction.

27. A method for monitoring the neuronal activity and dysfunction in a human patient, comprising:

(a) illuminating neuronal tissue with an illumination source emitting electromagnetic radiation (emr) having at least one wavelength of from about 450 nm to about 2500 nm;

(b) detecting one or more optical properties of the illuminated neuronal tissue and acquiring a baseline data set representing one or more of the optical properties detected;

(c) detecting one or more optical properties of the illuminated neuronal tissue at a time subsequent to acquisition of the baseline data set and acquiring a subsequent data set; and (d) comparing the subsequent data set with the baseline data set to identify changes in optical properties of the illuminated neuronal tissue that are indicative of neuronal activity or dysfunction.

* * * * *